United States Patent
Kisak et al.

(10) Patent No.: US 10,716,754 B2
(45) Date of Patent: Jul. 21, 2020

(54) TOPICAL FORMULATION

(71) Applicant: Tioga Research, Inc., San Diego, CA (US)

(72) Inventors: Edward Thomas Kisak, San Diego, CA (US); John Michael Newsam, La Jolla, CA (US); Servet Buyuktimkin, San Diego, CA (US); Nadir Buyuktimkin, San Diego, CA (US)

(73) Assignee: Tioga Research, Inc., San Diego, CA (US)

( * ) Notice: Subject to any disclaimer, the term of this patent is extended or adjusted under 35 U.S.C. 154(b) by 0 days.

(21) Appl. No.: 15/469,963

(22) Filed: Mar. 27, 2017

(65) Prior Publication Data

US 2017/0290769 A1 Oct. 12, 2017

Related U.S. Application Data

(60) Provisional application No. 62/390,369, filed on Mar. 28, 2016.

(51) Int. Cl.
| | |
|---|---|
| *A61K 31/197* | (2006.01) |
| *A61K 9/06* | (2006.01) |
| *A61K 47/10* | (2017.01) |
| *A61K 47/12* | (2006.01) |
| *A61K 47/14* | (2017.01) |
| *A61K 47/20* | (2006.01) |
| *A61K 45/06* | (2006.01) |
| *A61K 9/00* | (2006.01) |
| *A61K 47/32* | (2006.01) |
| *A61K 47/44* | (2017.01) |

(52) U.S. Cl.
CPC .............. *A61K 9/06* (2013.01); *A61K 9/0014* (2013.01); *A61K 31/197* (2013.01); *A61K 45/06* (2013.01); *A61K 47/10* (2013.01); *A61K 47/12* (2013.01); *A61K 47/20* (2013.01); *A61K 47/32* (2013.01); *A61K 47/44* (2013.01)

(58) Field of Classification Search
CPC ...... A61K 31/197; A61K 9/06; A61K 9/0014; A61K 47/10; A61K 47/12; A61K 47/14; A61K 47/20; A61K 47/32; A61K 47/44
See application file for complete search history.

(56) References Cited

U.S. PATENT DOCUMENTS

| | | | |
|---|---|---|---|
| 4,652,557 | A | 3/1987 | Sandborn |
| 7,045,145 | B1 * | 5/2006 | Chien .................. A61K 9/0014 424/443 |
| 8,252,838 | B2 | 8/2012 | Kisak et al. |
| 8,563,613 | B2 | 10/2013 | Kisak et al. |
| 8,871,809 | B2 | 10/2014 | Kisak et al. |
| 9,066,913 | B2 | 6/2015 | Kisak et al. |
| 9,101,591 | B2 | 8/2015 | Kisak et al. |
| 2009/0247635 | A1 | 10/2009 | Ehrenpreis |
| 2013/0211351 | A1 * | 8/2013 | Fuhrherr ............. A61K 9/7038 604/307 |
| 2013/0331803 | A1 | 12/2013 | Fleschhut et al. |
| 2014/0178459 | A1 | 6/2014 | Kisak et al. |

FOREIGN PATENT DOCUMENTS

WO WO-2009/133430 11/2009

OTHER PUBLICATIONS

Williams et al. Advanced Drug Delivery Reviews 2004, 56, 603-618.*
Som et al. J. Pharm. Bioall. Sci. 2012, 4 (1), 2-9.*
International Search Report and Written Opinion for PCT/US2017/024281 dated Jul. 31, 2017, 16 pages.
Ali et al., A streptozotocin-induced diabetic neuropathic pain model for static or dynamic mechanical allodynia and vulvodynia: validation using topical and systemic gabapentin. Naunyn Schmiedebergs Arch Pharmacol, Nov. 2015, 388(11), 1129-1140.
Arafa et al., DOE Optimization of Nano-based Carrier of Pregabalin as Hydrogel: New Therapeutic & Chemometric Approaches for Controlled Drug Delivery Systems. Sci Rep, Jan. 30, 2017, 7, 41503.
Baron, Neuropathic Pain: A Clinical Perspective. In B.J. Canning and D. Spina eds. *Sensory Nerves*. Springer Berlin Heidelberg, 2009, vol. 194, p. 3-30.
Bhatia et al., Formulation and Evaluation of Transdermal Patch of Pregabalin. International Journal of Pharmaceutical Sciences and Research, 2012, 3(2), 569-575.
Boardman et al., Topical gabapentin in the treatment of localized and generalized vulvodynia. Obstetrics and gynecology, 2008, 112(3), 579-585.
Brown, Prescribing flexibility through prescription compounding. Techniques in Regional Anesthesia and Pain Management, 2008, 12(2), 119-121.
Carlton et al. Attenuation of formalin-induced nociceptive behaviors following local peripheral injection of gabapentin. Pain, 1998, 76(1-2), 201-207.
Chen et al., Stereospecific Effect of Pregabalin on Ectopic Afferent Discharges and Neuropathic Pain Induced by Sciatic Nerve Ligation in Rats. Anesthesiology, 2001, 95(6), 1473-1479.

(Continued)

*Primary Examiner* — Irina Neagu
(74) *Attorney, Agent, or Firm* — Sheppard Mullin Richter & Hampton LLP

(57) ABSTRACT

Provided herein are topical formulations. The topical formulation may comprise: (i) pregabalin, (ii) water, (iii) DMSO, (iv) a keto acid, and (v) and/or a fatty alcohol. The topical formulation may also comprise (i) pregabalin, (ii) DMSO, (iii) a keto acid and (iv) a fatty acid ester. It has been discovered that the combinations of DMSO with a keto acid such as levulinic acid and/or and a fatty acid ester such as lauryl lactate, or combinations of DMSO with a keto acid such as levulinic acid and/or with a fatty alcohol such as oleyl alcohol are excellent penetration enhancers and, as such, can be incorporated in a skin-applied formulation to facilitate administration of pregabalin.

9 Claims, 11 Drawing Sheets

(56) References Cited

OTHER PUBLICATIONS

Davies et al., The prevalence, severity, and impact of painful diabetic peripheral neuropathy in type 2 diabetes. Diabetes Care, Jul. 2006, 29(7), 1518-1522.
Doddrell et al., Successful use of pregabalin by the rectal route to treat chronic neuropathic pain in a patient with complete intestinal failure. BMJ Case Rep, Oct. 29, 2015, 2015.
Dolphin, The α2δ subunits of voltage-gated calcium channels. Biochim Biophys Acta, 2013, 1828(7), 1541-1549.
Drolet et al., Predictors of postherpetic neuralgia among patients with herpes zoster: a prospective study. J Pain, Nov. 2010, 11(11), 1211-1221.
Dworkin et al., Pharmacologic management of neuropathic pain: Evidence-based recommendations. Pain, 2007, 132(3), 237-251.
Dworkin et al., Recommendations for the Pharmacological Management of Neuropathic Pain: An Overview and Literature Update. Mayo Clinic Proceedings, Mar. 1, 2010 2010, 85(3 suppl), S3-S14.
Foroutan et al., Role of Pregabalin in Management of Pruritus: A Literature Review. J Pharm Pharm Sci, Oct.-Dec. 2016, 19(4), 465-474.
Franz, Percutaneous absorption. On the relevance of in vitro data. J. Invest. Dermatol, 1975, 64, 190-195.
Fukasawa et al., Transdermal administration of aqueous pregabalin solution as a potential treatment option for patients with neuropathic pain to avoid central nervous system-mediated side effects. Biol Pharm Bull, 2014, 37(11), 1816-1819.
Hempenstall et al., Analgesic Therapy in Postherpetic Neuralgia: A Quantitative Systematic Review. PLoS Med, 2005, 2(7), 0628-0644.
Hiom et al., Severe postherpetic neuralgia and other neuropathic pain syndromes alleviated by topical gabapentin. British Journal of Dermatology, 2015, 173(1), 300-302.
International Search Report and Written Opinion for PCT/US2017/024281 dated Jul. 31, 2017, 11 pages.
Jensen et al., The clinical picture of neuropathic pain. European journal of pharmacology, 2001, 429(1-3), 1-11.
Matsuda et al., Gabapentin and pregabalin for the treatment of chronic pruritus. J Am Acad Dermatol, Sep. 2016, 75(3), 619-625. e616.
O'Connor et al., Treatment of Neuropathic Pain: An Overview of Recent Guidelines. The American Journal of Medicine, 2009, 122(10, Supplement 1), S22-S32.
Ostrenga et al., Significance of vehicle composition. I. Relationship between topical vehicle composition, skin penetrability, and clinical efficacy. J Pharm Sci, Aug. 1971, 60(8), 1175-1179.
B&B Pharmacy Compounding and Health Care Center, Pain Management Compounding, www.bbpharmacy.com, 2010.
Plaza-Villegas et al., Topical pregabalin and diclofenac for the treatment of neuropathic orofacial pain in rats. Oral surgery, oral medicine, oral pathology and oral radiology, 2012, 114(4), 449-456.
Prommer, Topical analgesic combinations for bortezomib neuropathy. J Pain Symptom Manage, Mar. 2009, 37(3), e3-5.
Sadosky et al., A review of the epidemiology of painful diabetic peripheral neuropathy, postherpetic neuralgia, and less commonly studied neuropathic pain conditions. Pain Pract, Jan.-Feb. 2008, 8(1), 45-56.
Shahid et al., Topical gabapentin gel alleviates allodynia and hyperalgesia in the chronic sciatic nerve constriction injury neuropathic pain model. Eur J Pain, Nov. 8, 2016, 21, 668-680.
Smith et al., Epidemiology of neuropathic pain and its impact on quality of life. Curr Pain Headache Rep, 2012, 16(3), 191-198.
Taxonomy, I. T. F. O. Part III: Pain Terms, A Current List with Definitions and notes on Usage. Seattle: I. Press, 1994.
Taylor et al., Pharmacology and mechanism of action of pregabalin: the calcium channel alpha2-delta (alpha2-delta) subunit as a target for antiepileptic drug discovery. Epilepsy research, 2007, 73(2), 137-150.
Tesfaye et al., Painful Diabetic Peripheral Neuropathy: Consensus Recommendations on Diagnosis, Assessment and Management. Diabetes/Metabolism Research and Reviews, 2011, 1-9.
Todorovic et al., Potent analgesic effects of anticonvulsants on peripheral thermal nociception in rats. British Journal of Pharmacology, 2003, 140(2), 255-260.
Torrance et al., The epidemiology of chronic pain of predominantly neuropathic origin. Results from a general population survey. J Pain, Apr. 2006, 7(4), 281-289.
Vinik, The approach to the management of the patient with neuropathic pain. J Clin Endocrinol Metab, Nov. 2010, 95(11), 4802-4811.
Weaver, The Burden of Herpes Zoster and Postherpetic Neuralgia in the United States. J Am Osteopath Assoc, Mar. 1, 2007 2007, 107(suppl_1), S2-7.
Yawn et al., The prevalence of neuropathic pain: clinical evaluation compared with screening tools in a community population. Pain Med, Apr. 2009, 10(3), 586-593.

* cited by examiner

TOPICAL FORMULATION

CROSS-REFERENCE TO RELATED APPLICATIONS

The application claims the benefit under 35 U.S.C. § 119(e) of U.S. Provisional Application 62/390,369, filed Mar. 28, 2016, which is hereby incorporated by reference in its entirety.

FIELD

The present disclosure relates to a topical formulation of a pharmaceutical agent comprising multiplexed molecular penetration enhancers.

BACKGROUND

The administration of a drug through the skin for systemic distribution, that is transdermally, can provide compelling advantages relative to other modes of administration. Transdermal administration circumvents potential complications in the gastrointestinal ("GI") tract, avoids first-pass metabolism in the liver, can allow delivery of an active ingredient with a relatively short biological half-life or a narrow therapeutic window, facilitates uniform plasma dosing of the active ingredient, and, as above, is broadly preferred from a user compliance perspective.

In spite of the advantages, transdermal administration is limited to only a small number of drugs. For example, a transdermal patch format is currently limited to some thirty drugs (including scopolamine, fentanyl, estradiol, nitroglycerin, nicotine, testosterone, selegiline and methyl phenidate). The reason for the paucity of transdermal products to treat serious pain conditions is that the skin presents a formidable barrier.

Structurally, the skin consists of two principle layers: (i) the epidermis, the outermost layer, which varies in thickness from 0.05 mm on the eyelids to 1.5 mm on the palms and soles of the feet but which typically averages 80 µm, and (ii) the 'dermis,' the inner region, ranges in thickness from 0.4 to 4 mm, with a typical average of 2 mm. The outermost layer of the epidermis (the 'stratum corneum') comprises corneocytes (flattened dead cells which are filled with keratin), interconnected by corneodesmosomes and surrounded by lipids which form lamellar phases. The highly impermeable nature of skin is due primarily to the stratum corneum. The viable epidermis underlying the stratum corneum is akin to other living tissue. The dermis provides the skin's structural strength as well as the nerve and vascular networks that support the epidermis.

Various factors can affect the skin absorption rates and penetration depths of a drug molecule applied in a formulation to the skin, including the nature of the active ingredient, the nature of the vehicle, the pH, and the relative solubility of the active in the vehicle versus the skin. More specifically, drug attributes such as solubility, size and charge, melting point as well as vehicle attributes such as the drug solubility and dissolution rate, ability to alter the membrane permeability, spreadability and adhesion can each have significant effects on permeability.

Delivering an active agent into or through the skin in sufficient concentrations usually requires some means for reducing the stratum corneum's hindrance to ingress of the active agent. A number of physical methods for lowering the stratum corneum's barrier properties have been developed including electrically assisted techniques such as iontophoresis or electroporation, ultrasound, heat, puncturing the stratum corneum with microneedle arrays, or ablation. Even for a single, non-repeated application such physical methods have limitations, leading to very restricted use by patients in practice.

SUMMARY

Some embodiments provide for a topical formulation comprising multiplexed molecular penetration enhancers for topical or transdermal administration of a zwitterionic pharmaceutical agent. In some embodiments, the present disclosure relates to a topical formulation comprising multiplexed molecular penetration enhancers for topical or transdermal administration of a gabapentinoid. In some embodiments, the present disclosure relates to a topical formulation comprising multiplexed molecular penetration enhancers for topical or transdermal administration of pregabalin.

In another of its aspects, the present disclosure provides a topical formulation for use in topical or transdermal administration of a substance comprising: (i) at least one active agent, (ii) DMSO, (iii) a keto acid, and (iv) a fatty acid ester.

In another of its aspects, the present disclosure provides a topical formulation comprising: (i) at least one active agent, (ii) water, (iii) dimethyl sulfoxide ("DMSO"), (iv) a keto acid, and (v) an ester of a fatty alcohol and an α-hydroxy acid, an ester of a fatty acid and an alcohol, or a mixture thereof.

In another of its aspects, the present disclosure provides a topical formulation comprising: (i) at least one active agent, (ii) water, (iii) DMSO, (iv) a keto acid, and (v) a fatty alcohol.

In another of its aspects, the present disclosure provides a topical formulation for use in topical or transdermal administration of a substance comprising: (i) at least one active agent, (ii) DMSO, (iii) levulinic acid, and (iv) lauryl lactate.

In another of its aspects, the present disclosure provides a topical formulation for use in topical or transdermal administration of a substance comprising: (i) at least one active agent, (ii) DMSO, (iii) a keto acid, (iv) a fatty acid ester, and (v) a polyalkylene glycol alkyl ether.

In another of its aspects, the present disclosure provides a topical formulation for use in topical or transdermal administration of a substance comprising: (i) at least one active agent, (ii) DMSO, (iii) levulinic acid, (iv) lauryl lactate, and (v) a polyethylene glycol alkyl ether.

In another of its aspects, the present disclosure provides a topical formulation for use in topical or transdermal administration of a substance comprising: (i) at least one active agent, (ii) DMSO, (iii) levulinic acid, (iv) lauryl lactate, and (v) dimethyl isosorbide.

In another of its aspects, the present disclosure provides a topical formulation for use in topical or transdermal administration of a substance comprising: (i) at least one active agent, (ii) DMSO, (iii) a fatty alcohol or a fatty acid ester, and (iv) a polyalkylene glycol alkyl ether.

In another of its aspects, the present disclosure provides a topical formulation for use in topical or transdermal administration of a substance comprising: (i) at least one active agent, (ii) DMSO, (iii) oleyl alcohol, and (iv) a polyalkylene glycol alkyl ether.

In another of its aspects, the present disclosure provides a topical formulation for use in topical or transdermal administration of a substance comprising: (i) at least one active agent, (ii) DMSO, (iii) lauryl lactate, and (iv) a polyalkylene glycol alkyl ether.

In another of its aspects, the present disclosure provides a topical formulation comprising: (i) at least one active agent, (ii) DMSO, (iii) a fatty alcohol or a fatty acid ester, (iv) a polyalkylene glycol alkyl ether, and (v) a keto acid.

In another of its aspects, the present disclosure provides a topical formulation comprising: (i) at least one active agent, (ii) DMSO, (iii) a fatty alcohol or a fatty acid ester, (iv) a polyalkylene glycol alkyl ether, and (v) levulinic acid.

In another of its aspects, the present disclosure provides a topical formulation comprising: (i) at least one active agent, (ii) DMSO, and (iii) a plurality of polyalkylene glycol alkyl ethers.

In one aspect, the at least one active agent is a zwitterionic active agent. In one aspect, the at least one active agent is a gabapentinoid.

Some embodiments provide for a topical formulation suitable for concentrating a zwitterionic active agent in dermal tissue comprising: (i) at least one zwitterionic active agent, (ii) water, (iii) DMSO, (iv) a keto acid, and (v) an ester of a fatty alcohol and an α-hydroxy acid, an ester of a fatty acid and an alcohol, or a mixture thereof.

In another of its aspects, the present disclosure provides a topical formulation suitable for concentrating a zwitterionic active agent in dermal tissue comprising: (i) at least one zwitterionic active agent, (ii) water, (iii) DMSO, (iv) a keto acid, and (v) a fatty alcohol.

Some embodiments provide for a topical formulation for use in topical or transdermal administration of pregabalin comprising: (i) pregabalin, (ii) DMSO, (iii) a keto acid, and (iv) a fatty acid ester.

In another of its aspects, the present disclosure provides a topical formulation comprising: (i) pregabalin, (ii) water, (iii) DMSO, (iv) a keto acid, and (v) an ester of a fatty alcohol and an α-hydroxy acid, an ester of a fatty acid and an alcohol, or a mixture thereof.

In another of its aspects, the present disclosure provides topical formulation comprising: (i) pregabalin, (ii) water, (iii) DMSO, (iv) a keto acid, and (v) a fatty alcohol.

In another of its aspects, the present disclosure provides a topical formulation for use in topical or transdermal administration of pregabalin comprising: (i) pregabalin, (ii) DMSO, (iii) levulinic acid, and (iv) lauryl lactate.

In another of its aspects, the present disclosure provides a topical formulation for use in topical or transdermal administration of pregabalin comprising: (i) pregabalin, (ii) DMSO, (iii) a keto acid, (iv) a fatty acid ester, and (v) a polyalkylene glycol alkyl ether.

In another of its aspects, the present disclosure provides a topical formulation for use in topical or transdermal administration of pregabalin comprising: (i) pregabalin, (ii) DMSO, (iii) levulinic acid, (iv) lauryl lactate, and (v) a polyethylene glycol alkyl ether.

In yet another of its aspects, the present disclosure provides a method for treating a subject suffering from pain, said method comprising the administration to an area of skin of said subject a therapeutically effective amount of formulation comprising: (i) pregabalin, (ii) DMSO, (iii) a keto acid, and (iv) a fatty acid ester, thereby preventing or ameliorating said pain.

In yet another of its aspects, the present disclosure provides a topical formulation comprising a therapeutically active agent, a therapeutically acceptable carrier and a skin molecular penetration enhancer, wherein the skin molecular penetration enhancer consists essentially of a mixture of (i) DMSO, (ii) a keto acid and (iii) a fatty acid ester.

In yet another of its aspects, the present disclosure provides a method for treating a subject suffering from pain, said method comprising the topical administration to said subject of a therapeutically effective amount of formulation comprising: (i) pregabalin, (ii) DMSO, (iii) a keto acid, and (iv) an ester of a fatty alcohol and an α-hydroxy acid, an ester of a fatty acid and an alcohol, or a mixture thereof. In some embodiments, the topical administration of the formulation prevents or ameliorates said pain.

In yet another of its aspects, the present disclosure provides a method for treating a subject suffering from pain, said method comprising the topical administration to said subject of a therapeutically effective amount of formulation comprising: (i) at least one zwitterionic active agent, (ii) water, (iii) DMSO, (iv) a keto acid and (v) an ester of a fatty alcohol and an α-hydroxy acid or a fatty alcohol, thereby preventing or ameliorating said pain. In some embodiments, the topical administration of the formulation prevents or ameliorates said pain.

These and other objects, aspects, and embodiments will become more apparent when read with the following detailed description and drawings.

DETAILED DESCRIPTION

Figure 1:
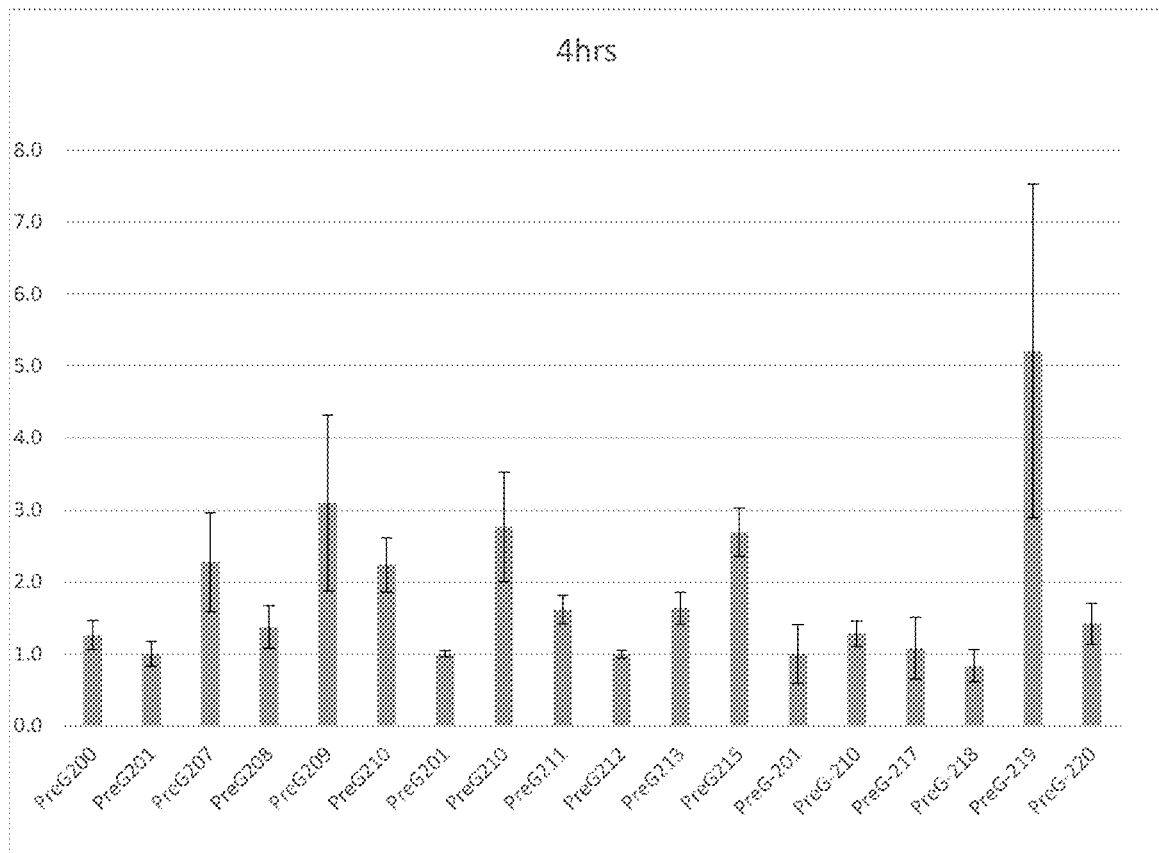
FIG. 1 illustrates enhancement ratios, computed as the ratios of cumulative amounts of pregabalin that are found to permeate through human skin over a 4 hour period from the formulations of Example 1 (Tables 1-5) relative to that measured in the same experiment from formulation TrPg201 (Table 1).
Figure 2:
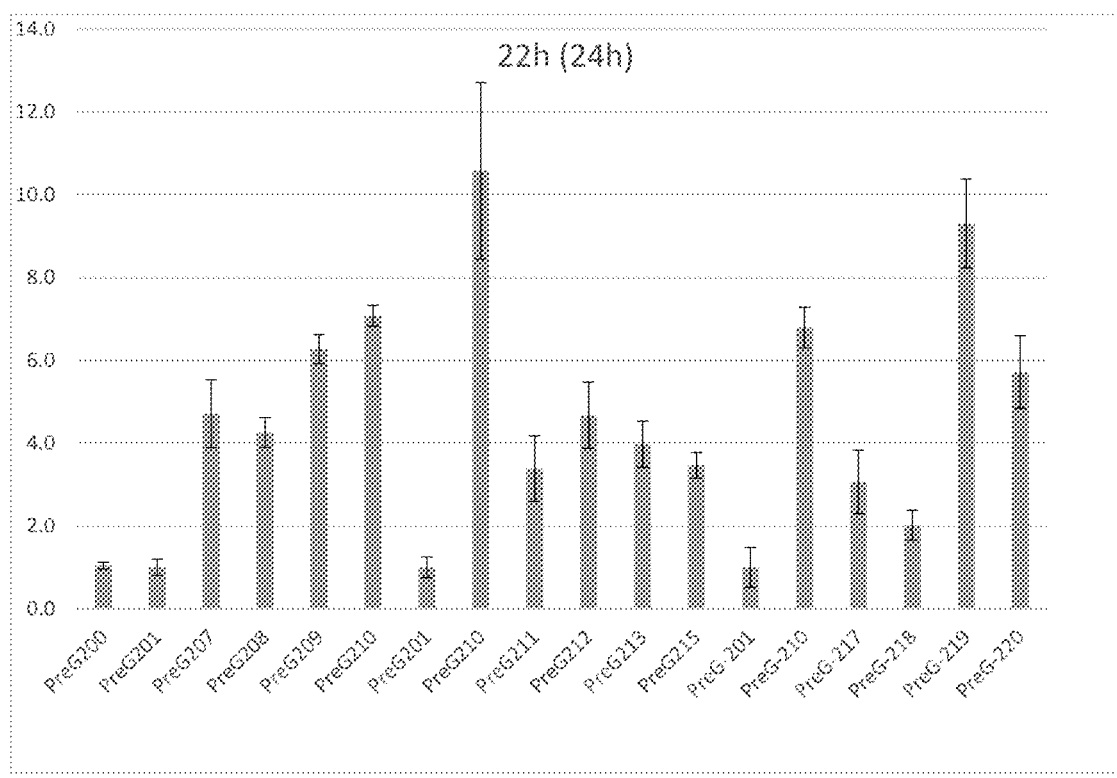
FIG. 2 illustrates enhancement ratios, computed as the ratios of cumulative amounts of pregabalin that are found to permeate through human skin over a 22 hour or 24 hour period from the formulations of Example 1 (Tables 1-5) relative to that measured in the same experiment from formulation TrPg201 (Table 1).
Figure 3:
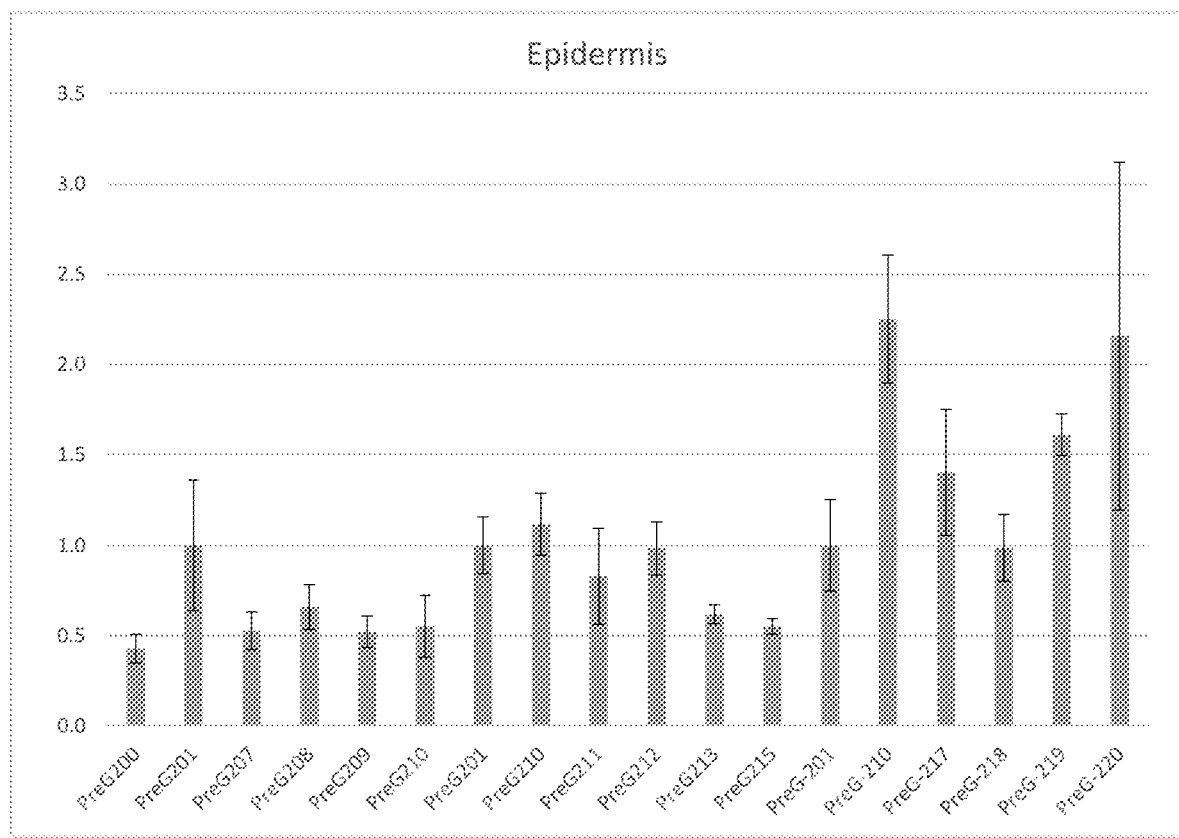
FIG. 3 illustrates enhancement ratios, computed as the ratios of amounts of pregabalin that are found to be retained in human epidermal tissue 22 hour or 24 hour after formulation application from the formulations of Example 1 (Tables 1-5) relative to that measured in the same experiment from formulation TrPg201 (Table 1).
Figure 4:
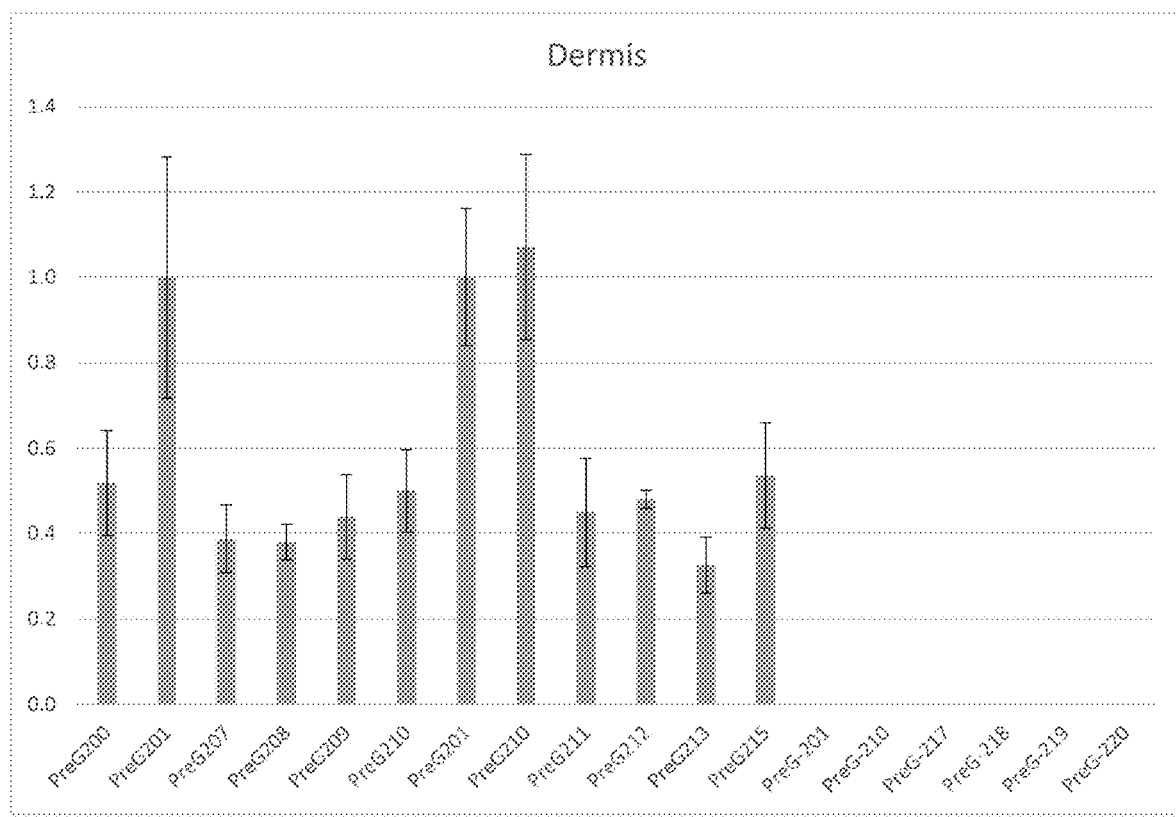
FIG. 4 illustrates enhancement ratios, computed as the ratios of amounts of pregabalin that are found to be retained in human dermal tissue 22 hour or 24 hour after formulation application from the Example 1 formulations (Tables 1-5) relative to that measured in the same experiment from formulation TrPg201 (Table 1). The blank columns at right indicate that the corresponding data were not measured.

Other than physical methods, it is well known in the art that various factors can affect the permeation and absorption of an active agent from a skin-applied pharmaceutical preparation, including the nature of the active, the nature of the vehicle, the pH, and the relative solubility of the active in the vehicle versus the skin. More specifically, active attributes such as molecular weight, lipophilicity or hydrophilicity, solubility, size and charge, melting point, as well as vehicle attributes such as active solubility and dissolution rate, ability to modulate the permeability of the stratum corneum, and physical characteristics such as occlusivity, spreadability and adhesion, and can each have significant effects on permeability.

Molecular or chemical penetration enhancers can provide an effective and inexpensive means of temporarily reducing skin resistance to the passage of actives and other molecules. Molecular penetration enhancers or "MPE™"s can enhance the diffusion of molecules across the skin by, for example, disrupting the lipid bilayers of the stratum corneum.

Over 300 substances have been identified as MPE™ s but few have been developed successfully into commercial formulations. Many potent enhancers are irritating to the cells of the epidermis which can limit both the choice and concentration of MPE™ s suitable for topical formulations. Discovery of new MPE™ s to increase skin permeability is desirable and has been an area of high activity over the last 30 years. However, the number of substances identified to be penetration enhancers is still tiny relative to the more than 127,000,000 substances identified in the CAS registry (Chemical Abstracts Service, Columbus, Ohio, www.cas.org). Further, for use in a drug product the excipients in a formulation should not introduce fresh safety or other regulatory concerns. It is therefore preferable that the choices of excipients be limited to those that are provided in the US Food and Drug Administration ("FDA") inactive ingredient database ("IID").

The number of candidate drugs suitable for topical and transdermal administration could be significantly increased with improved approaches to molecular penetration enhancement. Notably, it is now realized that the best permeation enhancement is typically found with combinations of MPETms, rather than by use of individual MPE™ s alone. Further, the penetration enhancing roles of neither individual MPE™ s nor of MPE™ combinations can be predicted.

Currently only two drugs for administration to the skin with a peripheral mode of action and little to no systemic activity, are currently FDA approved and recommended by authorities to treat peripheral neuropathic pain, namely a topical lidocaine patch 5% (Lidoderm®) and a topical capsaicin patch 8% (Qutenza®). This is despite a substantial and protracted global research effort. Even while such programs have yet to be successful, they serve as evidence of the major need for a novel way to treat peripheral neuropathic pain through a skin-applied administration route.

Additionally, literature data support a peripheral action for gabapentinoids. Analgesic effects on peripheral nociception in rats are demonstrated following administration of injectable gabapentin and these anti-hyperalgesic properties were shown not to be due to a systemic effect. Gabapentin has been postulated to offer a novel therapeutic option for local treatment of pain of peripheral origin.

Despite the appeal of an effective skin-applied formulation of a gabapentinoid, the art teaches little on development of such skin-applied formulations. Both gabapentin and pregabalin are zwitterionic (a zwitterion is a chemical compound that is electrically neutral through a net cancellation of formal positive and negative charges at different locations in the molecule) and have a very low intrinsic skin permeabilities.

Zwitterionic drugs have poor absorption through intact skin due to their rather large dipole moments and their resulting low lipid solubility. Non-zwitterionic acidic or basic substances can be placed in transdermal formulations at appropriate pH-values such that the active agent is substantially in the non-ionic form, leading to enhanced absorption through skin. Zwitterionic drugs cannot be made non-ionic. At all pH-values, at least one ionic group is present. For example, at pH-values higher than the pKa of the acidic group(s) of a zwitterion, the acidic group is charged; at pH-values lower than the pKa of the basic group(s) of a zwitterion, the basic group is charged. At pH-values close to the zwitterion isoelectric point ("pI"), both groups are charged. Amino acid containing drugs, being zwitterions of great interest, remain charged at all pH-values in the range of 2.0 to 11, spanning the pH-range that is suitable for transdermal application. It would not be expected that one could achieve a suitable flux of a zwitterion through the skin to make transdermal administration thereof practical.

A gabapentin paste (made by combining gabapentin in ethoxy diglycol with a commercial chassis, namely Lipoderm base (PCCA, Houston, Tex.)), prepared at 2%, 4%, or 6% strengths, is described; from a study of application to postmenopausal women patients it was concluded that topical gabapentin was well tolerated and associated with significant pain relief. Case reports teach the use of topical gabapentin formulated by pharmacists in conjunction with other pharmaceutical actives. Pregabalin has been administered rectally with anecdotal success. Applications of a topical gabapentin gel to alleviate allodynia and hyperalgesia in the chronic sciatic nerve constriction injury neuropathic pain model in rats by a topical gabapentin gel, to relieve postherpetic neuralgia, and to alleviate mechanical allodynia and vulvodynia in a rat model of streptozotocin-induced diabetic neuropathic nociception have each been reported.

A topical pregabalin formulated in a non-active vehicle of pluronic lecithin organogel and an anhydrous gel base was previously described; testing in a rat model of such a formulation at a 10% pregabalin strength provided a significant reduction of pain as well as significantly decreased pregabalin plasma levels as compared to the systemic treatment, suggesting both its efficacy and a peripheral mode of action. Preparation of niosomes (non-ionic surfactant-based vesicles) entrapping pregabalin were previously prepared and reportedly exhibited pregabalin fluxes of up to 117 μg $cm^{-2}$ $h^{-1}$ through excised rat skin at 37±0.5° C. Permeation of pregabalin through shaved abdominal rat skin from matrix type transdermal pregabalin patches, ostensibly over up to 30 days, has also been reported. The impact of transdermal administration of pregabalin from a simple aqueous pregabalin solution pain thresholds in rats has also been studied. Others have observed that topical treatment with 10% pregabalin or 5% diclofenac formulations impacts neuropathic orofacial pain in rats significantly. While human skin is dramatically less permeable than rodent skin, preventing an extrapolation of any of these reports to prospective performance in humans, these studies do underscore the interest in topical and transdermal formulations of gabapentinoids.

In light of the foregoing, there is a need for a formulation suitable for skin administration that can provide more substantial levels of delivery of a zwitterionic pharmaceutical gabapentinoid into and through the skin of a subject.

The present disclosure satisfies these and other needs. It has surprisingly and unexpectedly been discovered that certain combinations of compounds are excellent molecular penetration enhancers for pregabalin and for other active agents and, as such, can be incorporated in a topical formulation to facilitate administration of pregabalin or of one or more other active ingredients. The increased penetration enhancement can also lead to a reduction in the total concentration of skin irritants in a formulation.

I. Definition of Terms

The terms "a," "an," or "the" as used herein not only include aspects with one member, but also includes aspects with more than one member. For example, an embodiment including "a cellulosic thickening agent and a lower monohydric alcohol" should be understood to present certain aspects with at least a second cellulosic thickening agent, at least a second lower monohydric alcohol, or both. An embodiment including "an active agent" should be understood to present certain aspects with at least a second active agent, which may be of a different class (e.g., a non-steroidal anti-inflammatory drug with an anti-inflammatory steroid or a local anesthetic).

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X". When the quantity "X" only includes whole-integer values (e.g., "X carbons"), "about X" indicates from (X−1) to (X+1). In this case, "about X" as used herein specifically indicates at least the values X, X−1, and X+1. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

In compositions comprising an "additional" or "second" component, the second component as used herein is chemically different from the other components or first component. A "third" component is different from the other, first, and second components, and further enumerated or "additional" components are similarly different.

"Agent" as used herein indicates a compound or mixture of compounds that, when added to a pharmaceutical composition, tend to produce a particular effect on the said composition's properties. For example, a composition comprising a thickening agent is likely to be more viscous than an otherwise identical comparative composition that lacks the thickening agent.

"Cellulosic thickening agent" as used herein includes a thickening agent that is a natural or synthetic polymeric carbohydrate (e.g., cellulose and pharmaceutically acceptable vegetable gums) or a polymeric or oligomeric derivative of a polymeric carbohydrate that is produced by chemical modification (e.g., hydroxypropyl cellulose, hydroxypropyl methyl cellulose, hydroxyethyl cellulose). Representative cellulosic thickening agents include cellulose, hydroxypropyl cellulose ("HPC"), hydroxypropyl methyl cellulose ("HPMC"), hydroxyethyl cellulose ("HEC"), methyl cellulose, carboxymethyl cellulose, and the like.

The terms "chassis," "vehicle" and "base formulation" as used interchangeably herein are equivalent terms that include a plurality of solvents or other excipients that comprise the bulk of a formulation, into which one or more active agents or additional components might be introduced.

As used herein, the phrase "effective amount" or "effective dose" means an amount sufficient to achieve the desired result and accordingly will depend on the ingredient and its desired result. Nonetheless, once the desired effect is known, determining the effective amount is within the skill of a person skilled in the art.

"Enhancement ratio" or "ER" as used interchangeably herein is the ratio of a test result (e.g., accumulated dose of product expressed in μg $cm^{-2}$) from a formulation comprising an active to the corresponding test result from a control composition comprising the same active at the same concentration in the formulation.

In general, the "error bars" on the graphs represent the standard error of the mean value, whereas the top of the solid, shaded bar represents a single data value, which is the mean value of the distribution of data values.

"Finite dosing" as used herein generally includes an application of a limited reservoir of an active agent. The active agent in the reservoir is depleted with time, leading to a decrease of the absorption rate after a maximum rate is reached.

"Formulation," "pharmaceutical composition," and "composition" as used interchangeably herein are equivalent terms referring to a composition of matter for pharmaceutical use.

"Local delivery" as used herein means delivery of an agent into the skin; in the literature such local delivery is frequently referred to as 'topical delivery.'

The prefix "micro" as used herein can be alternatively abbreviated as "μ" or "u." For example, micrograms are typically abbreviated as μg, but can alternatively be abbreviated as "ug".

"Monohydric alcohol" as used herein includes straight- or branched-chain alkyl alcohols with a single hydroxyl group. Representative monohydric alcohols include methanol, ethanol, n-propanol, isopropanol, n-butanol, t-butanol, n-pentanol, 3-pentanol, 2-methoxyethanol, 2-(2-ethoxyethoxy)ethanol (transcutol), oleyl alcohol, and the like.

As used herein the term "multiplexed molecular penetration enhancer" or "MMPE™" means a molecular penetration enhancer comprising two or more substances wherein each of the two or more substances is also a molecular penetration enhancer.

The term "or" as used herein should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

"Penetration enhancer," "molecular penetration enhancer" or "MPE™" as used herein includes an agent or a combination of agents that improves the transport of molecules such as a pharmaceutically or cosmetically active agent into or through a natural membrane such as skin or nail. Various conditions may occur at different sites in the body, either in the skin or below the skin, creating a need to target delivery of compounds. For example, in products designed to produce artificial tans delivery of a dye substance into the stratum corneum may be advantageous. A psoriasis treatment on the other hand may require delivery of therapeutic drug levels into deeper epidermal tissue. In a treatment for osteoarthritis delivery of the active agent into deeper underlying joint tissue may be necessary to achieve therapeutic benefit. In yet other applications, for example in hormone replacement therapy, delivery of drug to the systemic circulation may be an objective. Thus, a "molecular penetration enhancer" may be used to assist in the delivery of an active agent directly to the skin or underlying tissue or indirectly to the site of the disease through systemic distribution. If systemic distribution of an active agent (e.g., pregabalin) would be likely to produce side effects, a molecular penetration enhancer is selected to maximize direct delivery and to minimize systemic distribution. A penetration enhancer may be a pure substance or may comprise a mixture of different chemical entities. In this specification the terms "penetration enhancer," "chemical penetration enhancer," "molecular penetration enhancer," and "MPE™" or "MPE" are used interchangeably.

The term "pH adjusting agent" as used herein refers to a compound added to a composition as described herein for the purpose of changing the pH of the composition.

Examples of such agents include pharmaceutically acceptable acids, pharmaceutically acceptable bases, and pharmaceutically acceptable buffers.

The term "pharmaceutically acceptable" means compatible with the treatment of animals, and in particular, humans.

The term "pharmaceutically acceptable salt" means a pharmaceutically acceptable acid addition salt or a pharmaceutically acceptable base addition salt. The formation of a desired compound salt is achieved using standard techniques. For example, the neutral compound is treated with an acid or base in a suitable solvent and the formed salt is isolated by filtration, extraction, or any other suitable method.

"Regional delivery" as used herein means delivery of an agent through the skin but concentrating in proximal tissue or joint.

The term "subject" as used herein includes all members of the animal kingdom, preferably mammals, and most preferably, humans.

"Superficial delivery" as used herein means delivery of an agent to the skin exterior surface only.

"Surfactant" as used herein includes a surface-active agent. Surfactants reduce the surface tension of a solvent in which they are dissolved.

"Thickening agent" as used herein includes an agent or combination of agents that increases the viscosity of a composition. A thickening agent may be a pure substance, or it may comprise, consist essentially of, or consist of a mixture of different chemical entities. Exemplary thickening agents include cellulosic thickening agents, other polysaccharides such as chitosan and the like, carbomer polymers, carbomer derivatives, polyvinyl alcohol, poloxamers, as well as mixtures thereof.

"Topical formulation" as used herein includes a composition that is suitable for topical application to the skin, nail, or mucosa. A topical formulation may, for example, be used to confer a therapeutic or cosmetic benefit to its user. Specific topical formulations can be used for superficial, local, regional, or transdermal delivery of substances.

The term "topical administration" is used in its conventional sense to mean delivery of a substance, such as a therapeutically active agent, to the skin or to a localized region of the body.

Topical administration of a drug may often be advantageously applied in, for example, the treatment of various skin disorders.

"Transdermal" as used herein includes a process that occurs through the skin. The terms "transdermal," "percutaneous," and "transcutaneous" can be used interchangeably. In certain embodiments, "transdermal" may also include epicutaneous.

"Transdermal application" or "transdermal administration" as used interchangeably herein are equivalent terms that include administration through the skin. Transdermal application can be used for systemic delivery of an active agent. In certain embodiments, "transdermal application" may also include epicutaneous application.

The term "treating" or "treatment" as used herein (and as well understood in the art) means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the patient. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

The term "w/w" or "wt/wt" means a percentage expressed in terms of the weight of the ingredient or agent over the total weight of the composition multiplied by 100.

II. Constituents

A. Active Agent

The present disclosure provides for compositions and formulations comprising at least one active agent.

In one aspect, the at least one active agent is a zwitterionic active agent. Non-limiting examples of zwitterionic active agents include (4-{2-[2-hydroxy-2-(2-trifluoromethyl-thiazol-4-yl)-ethylamino]-propyl}-phenoxy)-acetic acid; (Z)-4-[(2-{[4-(2-chlorophenyl)-3-(ethoxycarbonyl)-5-(methoxycarbonyl)-6-methyl-1,4-dihydro-2-pyridinyl] methoxy}ethyl)amino]-4-oxo-2-butenoic acid; 2-(cyclohexylamino)ethanesulphonic acid ("CHES"); 2(N-morpholino)ethanesulphonic acid ("MES"); 2-azabicyclo-[3.3.0]-octane-3-carboxylic acids; 3-(cyclohexylamino) propanesulphonic acid ("CAPS"); 3-(N-morpholino) propanesulphonic ("MOPS"); 4-amino-3-phenylbutyric acid; 7-(6-amino-3-aza-bicyclo[3.1.0]hex-3-yl)-1-(2,4-difluoro-phenyl)-6-fluoro-4-oxo-1,4-dihydro-[1,8]naphthyridine-3-carboxylic acid; amino acids such as L-tyrosine or peptides; baclofen; benazeprilat; cefaclor; cefalexine; cefatrizine; cefdinir; cefepine; cefixime; cefpodoxime; cefroxadine; ceftriaxone; cephalosporin; cetirizine; cis, endo-2-azabicyclo-[3.3.0]-octane-3-carboxylic acids; cyclopropyl-8-(difluoromethoxy)-7-[(1R)-1-methyl-2,3-dihydro-1H-5-isoind-olyl]-4-oxo-1,4-dihydro-3-quinolinecarboxylic acid methanesulfonate monohydrate (bis-quinolone); diiodotyrosine; fexofenadine; gabapentin; heterocyclic selenates; L-dopa; levocetirizine; levothyrosine; libenzapril; liothyronin; melphalen; metironine; N-(2-acetamido) iminodiacetic acid ("ADA"); N-(2-acetamido)-2-aminoethanesulphonic acid (ACES); N,N-bis(2-hydroxyethyl)-2-aminoethanesulphonic acid ("BES"); N-2-hydroxyethylpiperazine-N'-2-ethanesulphonic acid ("HEPES"); N-2-hydroxyethylpiperazine-N'3-propanesulphonic acid ((H)EPPS); N-N[tris(hydroxymethyl)-methyl]-2-aminoethanesulphonic acid ("TES"); ofloxacin; p-aminosalicyclic acid; piperazine-N,N' bis(2-ethanesulphonic acid ("PIPES"); piro-2-aza-alkane-3-carbonitriles per U.S. Pat. No. 4,515,960; pregabalin; salicylates, such as cholinemagnesium salicylate; taurine (2-aminoethanesulphonic acid); α-methyldopa; and γ-aminobutyric acid ("GABA"). In some embodiments, the zwitterionic active agent is a gabapentinoid.

In some embodiments, the at least one active agent is an aryl alkanoic acid.

In one embodiment, the at least one active agent is a pharmaceutical agent, a cosmeceutical agent, a cosmetic agent, a nutritional supplement, a vitamin, a diagnostic agent, or an ink or colorant.

In one aspect, the at least one active agent is a gabapentinoid, that is, a 3-substituted derivative of the neurotransmitter GABA which blocks the α2δ subunit-containing voltage-dependent calcium channels ("VDCC"s). Non-limiting examples of gabapentinoids include gabapentin, pregabalin, mirogabalin, atagabalin, 4-methylpregabalin, F-phenibut, phenibut and PD-217,014. Also included are gabapentin prodrugs, such as gabapentin enacarbil. In some embodiments, the gabapentinoid is gabapentin, pregabalin, mirogabalin, atagabalin, 4-methylpregabalin and PD-217,014.

Gabapentin and pregabalin selectively interact with the α2δ subunit of voltage-dependent calcium channels ("VDCC"s) in the central nervous system. Gabapentin and pregabalin decrease the release of neurotransmitters such as glutamate, noradrenaline, and substance P, and increase neuronal γ-aminobutyric acid ("GABA") levels by producing a dose-dependent increase in glutamic acid decarboxylase activity. Gabapentin and pregabalin have potential in treatment of chronic pruritus. Gabapentin and pregabalin are also anticonvulsants. As transdermal administration is a very convenient modality and as patient compliance for transdermal administration surpasses those for other modalities, a formulation able to deliver gabapentin or pregabalin transdermally would be especially desired. Further, pregabalin has side effects when taken orally such as dizziness, sleepiness, dry mouth, blurred vision, difficulty with concentration, hyper-sensitivity and decreased platelet count; severe flatulence is also a known side effect of oral pregabalin.

In some embodiments, the active agent is a gabapentinoid. In some embodiments, the active agent is gabapentin or pregabalin. In one aspect, the active agent is pregabalin. In one aspect, the active agent is gabapentin.

The structures of pregabalin and gabapentin are shown below.

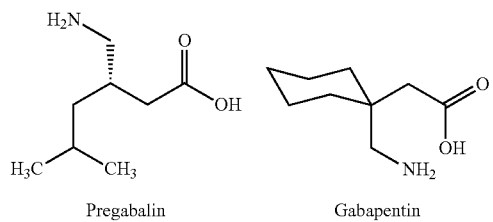

Pregabalin  Gabapentin

In one aspect, the at least one active agent is an anti-inflammatory agent. In some embodiments, the at least one active agent is a non-steroidal anti-inflammatory drug ("NSAID").

Non-limiting examples of NSAIDs include acetic acid derivatives such as indomethacin, sulindac, etodolac, and diclofenac; propionic acid derivatives such as pregabalin, naproxen, fenoprofen, ketoprofen, fluriprofen, and oxaprozin; coxibs such as celecoxib, rofecoxib, valdecoxib, parecoxib, lumiracoxib, and etoricoxib; fenamic acid derivatives such as mefenamic acid, meclofenamic acid, flufenamic acid, and tolfenamic acid; enolic acid derivatives such as piroxicam, meloxicam, tenoxicam, droxicam, and isoxicam; and the compounds' pharmaceutically acceptable salts such as diclofenac sodium, naproxen sodium, and diclofenac potassium and the like. In some embodiments, the NSAID is an acetic acid derivative or a pharmaceutically acceptable salt thereof, or a coxib or a pharmaceutically acceptable salt thereof. Other NSAIDs include aspirin, salicylic acid, diflunisal, etodolac, nabumetone, salsalate, and their pharmaceutically acceptable salts.

In some embodiments, the at least one active agent is an NSAID selected from the group consisting of acetaminophen (paracetamol), aspirin, celecoxib, diflunisal, etoricoxib, piroxicam, salsalate and rofecoxib, and pharmaceutically acceptable salts and solvates thereof, and mixtures thereof.

In some embodiments, the at least one active agent is a phenethylamine. In some embodiments, the active agent is a steroid.

An embodiment including "an active agent" should be understood to present certain aspects with at least a second active agent, which may be the same class or a different class (e.g., a gabapentinoid with a non-steroidal anti-inflammatory drug, or with an anti-inflammatory steroid, or with a local anesthetic).

Accordingly, in some embodiments, the formulations described herein comprise a combination of active agents, wherein the active agents are as described herein.

B. Dimethyl Sulfoxide ("DMSO")

In one aspect, the compositions and formulations comprise DMSO. DMSO is a polar aprotic solvent characterized as having low surface tension. DMSO permeates readily through skin and is known to function in some instances as a penetration enhancer. For example, while pharmaceutical compositions comprising DMSO have been reported, preferred embodiments, in certain of these cases comprise 50% w/w or higher of DMSO.

In the present disclosure, the DMSO may be present in an amount of 10% to 40% w/w. In some embodiments, DMSO is present in an amount of at least 12% w/w. In some embodiments, DMSO is present in an amount of at least 15% w/w. In some embodiments, DMSO is present in an amount of about 15-20% w/w. In a particular embodiment of the disclosure, DMSO is used at a concentration of about 12 to 20% w/w, such as 20, 21, 22, 23, 24, 25, 26, 27, 28, 29, 30, 31, 32, 33, 34 and 35 w/w as well as all fractions in between such as 22.5, 23.5, 24.5, 25.5, and the like.

C. Keto Acid

In one aspect, the compositions and formulations comprise a keto acid.

In the present disclosure the keto acid may be an alpha-keto acid (also known as "aka" a 2-oxoacid), such as pyruvic acid or oxaloacetic acid, a beta-keto acid (aka a 3-oxoacid), such as acetoacetic acid, or a gamma-keto acid (aka a 4-oxoacid), such as levulinic acid. In some embodiments, the keto acid is a gamma-keto acid. In some embodiments, the gamma-keto acid is levulinic acid.

In some embodiments, the keto acid is levulinic acid. Levulinic acid is present in an amount of up to about 10% w/w. In some embodiments, levulinic acid is present in an amount of up to about 5% w/w. In some embodiments, levulinic acid is present in an amount of up to about 2% w/w.

D. Fatty Acid Ester

In one aspect, the compositions and formulations comprise a fatty acid ester.

In the present disclosure, the fatty acid ester may be an ester resulting from the combination of a saturated fatty acid (such as, without limitation, caprylic acid, capric acid, lauric acid, myristic acid, palmitic acid, stearic acid, arachidic acid or behenic acid) or an unsaturated fatty acid (such as, without limitation, myristoleic acid, palmitoleic acid, sapienic acid, oleic acid, erucic acid, elaidic acid, vaccenic acid, linoleic acid, linoelaidic acid, α-linolenic acid, arachidonic acid or eicosapentaenoic acid) with a monohydric, dihydric or trihydric alcohol. In some embodiments, the fatty acid ester is an ester resulting from the combination of a fatty acid with a monohydric alcohol. In some embodiments, the fatty acid ester is an ester resulting from the combination of a saturated fatty acid with a monohydric alcohol. In some embodiments, the fatty acid ester is an ester resulting from the combination of a fatty alcohol with a hydroxy acid. In some embodiments, the fatty acid ester is an ester resulting from the combination of a saturated fatty alcohol with a hydroxy acid. In some embodiments, the fatty acid ester is an ester resulting from the combination of a saturated fatty alcohol with an α-hydroxy acid.

In some embodiments, the ester of a fatty alcohol and an α-hydroxy acid is lauryl lactate. In some embodiments, the fatty acid ester is lauryl lactate. Lauryl lactate is present in an amount of up to about 10% w/w. In some embodiments, lauryl lactate is present in an amount of up to about 5% w/w. In some embodiments, lauryl lactate is present in an amount of up to about 3% w/w.

In some embodiments, the fatty acid ester is an ester of a fatty acid and an alcohol. In some embodiments, the ester of a fatty acid and an alcohol is isopropyl myristate.

E. Fatty Alcohol

In one aspect, the compositions and formulations comprise a fatty alcohol.

In the present disclosure the fatty alcohol may include 1-octanol (aka capryl alcohol), 1-nonanol (aka pelargonic alcohol), 1-decanol (aka capric alcohol), 1-undecanol (aka undecyl alcohol), 1-dodecanol (aka lauryl alcohol), 1-tridecanol, 1-tetradecanol (aka myristyl alcohol), 1-pentadecanol (aka pentadecyl alcohol), 1-hexadecanol (aka cetyl alcohol), cis-9-hexadecen-1-ol (aka palmitoleyl alcohol), heptadecyl alcohol (aka 1-n-heptadecanol), 1-octadecanol (aka stearyl alcohol), cis-9-octadecen-1-ol (aka oleyl alcohol), 1-nonadecanol (aka nonadecyl alcohol), 1-eicosanol (aka arachidyl alcohol). In some embodiments, the fatty alcohol is oleyl alcohol. Oleyl alcohol is present in an amount of up to about 10% w/w. In some embodiments, oleyl alcohol is present in an amount of up to about 5% w/w. In some embodiments, oleyl alcohol is present in an amount of up to about 3% w/w.

F. Polyalkylene Glycol Alkyl Ether

In one aspect, the composition or formulation comprises at least one pharmaceutically acceptable surfactant that is a polyalkylene glycol alkyl ether. The polyalkylene glycol alkyl ether may be present at up to about 7% w/w, such as about 0.1, 0.15, 0.2, 0.3, 0.4, 0.5, 1.0, 1.5, 2, 2.5, 3, 3.5, 4, 4.5, 5, 5.5, 6, 6.5 or 7% w/w. In some embodiments, the polyalkylene glycol alkyl ether is present at up to about 2% w/w, such as about 0.1, 0.15, 0.2, 0.3, 0.4, 0.5, 1.0, 1.25, 1.5, 1.75 or 2% w/w.

In some embodiments, the composition or formulation comprises a polyalkylene glycol alkyl ether. In some embodiments, the composition or formulation comprises polyalkylene glycol alkyl ether such as a polypropylene oxide alkyl ether or a polyethylene glycol alkyl ether. Some non-limiting examples of polyalkylene glycol alkyl ethers include poly(oxyethylene) cetyl ether, poly(oxyethylene) palmityl ether, polyethylene oxide hexadecyl ether, polyethylene glycol cetyl ether, Brij™ 30 (Brij™ L4), Brij 38, Brij 52, Brij 56, Brij 58, Brij 78, Brij 98, Brij 700, Brij 700P, Brij 721, Brij S20, and Brij W1. In some embodiments, the polyalkylene glycol alkyl ether is a polyethylene glycol alkyl ether. In some embodiments, the polyalkylene glycol ether is a Brij polyalkylene glycol alkyl ethers.

Other non-limiting examples include members of the class of alkyl ether nonionic surfactants with two to 100 alkylene glycol repeat units in their polyalkylene glycol polymeric chains. In some embodiments, the alkyl group is derived from a fatty acid alcohol. In some embodiments, the polyalkylene glycol is polyethylene glycol.

The composition may include a polyalkylene glycol block co-polymer such as Poloxamer 188 or Poloxamer 407.

G. Alcohol

In one aspect, the compositions and formulations comprise a monohydric alcohol. Suitable monohydric alcohols include, but are not limited to, ethanol, propanol, propan-2-ol, (isopropanol), butanol, butan-2-ol (isobutanol), pentanol, pentan-2-ol, pentan-3-ol, 3-methyl-2-butanol, hexanol, hexan-2-ol, hexan-3-ol, benzyl alcohol, 2-(2-Ethoxyethoxy) ethanol (transcutol) and the like, as well as a mixture thereof.

In certain aspects, the monohydric alcohol is ethanol or benzyl alcohol.

In one aspect, the compositions and formulations comprise a diol. Suitable diols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, propylene glycol, and the like, as well as a mixture thereof. In one aspect, the formulation comprises about 0% to 20% w/w of a diol or about 5 to 15% of a diol. In certain aspects, the diol is a glycol, such as ethylene glycol, propylene glycol, or a mixture thereof. In some embodiments, the diol is propylene glycol.

In still another aspect, the composition or formulation includes at least two alcohols. In some embodiments, the formulation includes a monohydric alcohol and a diol. In some embodiments, the monohydric alcohol is ethanol. Alternatively, the diol is propylene glycol. In some embodiments, the monohydric alcohol is ethanol, and the diol is propylene glycol.

In one aspect, the compositions and formulations comprise a polyhydric alcohol. Suitable polyhydric alcohols include, but are not limited to glycerol, erythritol, threitol, arabitol, xylitol, ribitol and the like, as well as a mixture thereof.

In certain aspects, the polyhydric alcohol is glycerol (aka glycerin).

H. Additional Molecular Penetration Enhancer ("MPE™")

In one aspect, the composition or formulation comprises at least one additional pharmaceutically acceptable MPE™. Suitable MPE™ s include, but are not limited to, 2-amino-2-methyl-1-propanol, butyl alcohol, sodium lauryl ether(2) sulfate, cetearyl alcohol, chlorobutanol (1,1,1 trichloro-2-methyl-2-propanol), chloro-m-cresol, 4-chloro-3,5-dimethylphenol (chloroxylenol), disodium cocamphodiacetate, dioctyl phthalate, disodium laureth sulfosuccinate, 2-ethyl-1,3-hexanediol, ethyl oleate, ethanol, glyceryl laurate (glycerol monolaurate), glyceryl oleate (glycerol monooleate), glyceryl palmitate (monopalmitin), glyceryl ricinoleate, isopropyl myristate, isopropyl alcohol, lactic acid, lauric diethanolamide, L-a-lecithin, myristyl alcohol (tetradecanol), disodium lauryl sulfosuccinate, menthol, methyl laurate, sodium cocoyl sarcosinate (perlastan c 30), n-lauroyl sarcosine, octyl dodecanol, oleic acid (octadecenoic acid), propylene glycol, propylene glycol diacetate, propylene glycol dicaprylate, phenoxyethanol, sodium dodecyl benzene sulfonate, sodium lauryl ether sulfate, sodium dodecyl sulfate, sodium lauryl sulfoacetate, sodium n-lauroyl sarcosinate, Span 20 (sorbitan monolaurate), Span 80 (sorbitan monooleate), tertiary butanol, alpha-terpineol, triethanolamine lauryl sulfate, Tween 20 (POE sorbitan monolaurate), Tween 40 (POE sorbitan monopalmitate), Tween 60 (POE sorbitan monolaurate), Triton x (octoxynol 9), wickenol 143 (oleyl oleate), anise oil, laurocapram, benzyl dimethyl dodecyl ammonium bromide, polyethylene glycol dodecyl ether (PEGE), cocamidopropyl betaine (CBC), cocamidopropyl hydroxysultaine, oleyl betaine, cineole, cetyl trimethyl ammonium bromide, cyclopentadecanolide, dodecyl amine, dodecyl methyl sulfoxide, n-dodecyl-2-pyrrolidone, n-decyl-2-pyrrolidone, dimethyl sulfoxide, dodecyl pyridinium chloride, eucalyptus oil, glyceryl caprylate, glyceryl dilaurate, 1,2 hexanediol, hexadecyl dimethyl ammoniopropane sulfonate, potassium cocoyl hydrolyzed collagen, lauric acid, lauroylcholine chloride, limonene, linoleic acid, linolenic acid, lauryl lactate, 1-methyl-2-pyrrolidone, methyl salicylate, nicotine sulfate, octyl salicylate, octyl trimethyl ammonium bromide, poly(ethylene glycol) 300, 1-phenyl piperazine, salicylic acid, sodium cocoyl glutamate, sodium oleate, sodium octyl sulfate, TEA cocoyl hydrolyzed collagen, tetracaine, alpha-tocopherol and the like, as well as a mixture thereof.

In certain aspects, the additional MPE™ is dimethyl isosorbide.

I. Quaternary Ammonium Compound

In one aspect, the composition or formulation comprises at least one pharmaceutically acceptable long-chain quaternary ammonium compound. The long-chain quaternary ammonium compound serves as a surfactant and functions also as an antimicrobial (as per following). In certain aspects, the quaternary ammonium compound is cetylpyridinium chloride ("CPC") or cetylpyridinium bromide.

In certain aspects, the quaternary ammonium compound is cetylpyridinium chloride. The CPC may be present at up to about 7% w/w, such as about 0.1, 0.15, 0.2, 0.3, 0.4, 0.5, 1.0, 1.5, 2, 2.5, 3, 3.5, 4, 4.5, 5, 5.5, 6, 6.5 or 7% w/w. In some embodiments, the CPC is present at up to about 2% w/w, such as about 0.1, 0.15, 0.2, 0.3, 0.4, 0.5, 1.0, 1.25, 1.5, 1.75 or 2% w/w.

J. Water

In certain aspects, the compositions or formulations comprise water. In some embodiments, water is present from about 10% to 95% w/w such as about 10, 15, 20, 25, 30, 35, 40, 45, 50, 55, 60, 65, 70, 75, 80, 85, 90 or 95% w/w. In some embodiments, the composition includes from about 10 to 20%, about 20 to 40%, about 40 to 50%, about 50 to 60%, about 60 to 70%, or about 70 to 95% w/w water. Alternatively, the mixture includes about 10, 12.5, 15, 17.5, 20 or 25% w/w water.

K. Thickening Agent

In one aspect, the viscosity of the compositions and formulations is adjusted by incorporation of a thickening agent such as a cellulosic thickening agent, another polysaccharide such as chitosan or the like, a carbomer polymer, a carbomer derivative, polyvinyl alcohol, a poloxamer, or a mixture thereof and the like.

The nature of the thickener and the thickener concentration is chosen so as to produce a formulation of the desired viscosity, as is familiar to one skilled in the art.

L. Emollients

Emollients can optionally be added to the compositions or formulations of the disclosure so that the formulations can maintain or increase the moisture content of the stratum corneum when the composition is applied to the skin. Emollients may be added to the formulations in addition to the components already described, which may also aid in maintaining or improving the skin condition of the user.

In one aspect, added emollients are included in the compositions or formulations of the disclosure at a concentration between about 0.1 and 20% w/w. In another aspect, the added emollient can be present in the composition at a concentration between about 0.5% and 10% w/w. In still another aspect, the emollient concentration can be between about 1% and 5% w/w.

Emollients are generally separated into two broad classes based on their function. The first class of emollients functions by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

Suitable emollients may be selected from any of the classes known in the art. A general list of useful emollients appears, for example, in U.S. Pat. No. 4,478,853 and in EP patent application 0 522 624A1 as well as in the CTFA Cosmetic Ingredient Handbook published by The Cosmetic, Toiletry, and Fragrance Association, Washington D.C. (1992) under the listings "Skin Conditioning agents," "emollients," "humectants," "miscellaneous," and "occlusive."

In some aspects, emollients may be chosen from the following non-limiting list of general emollients, occlusive emollients, and humectants. Examples of general emollients include short-chain alkyl or aryl esters (C1-C7) of long-chain straight- or branched-chain alkyl or alkenyl alcohols or acids (C8-C32) and their polyethoxylated derivatives; short-chain alkyl or aryl esters (C1-C7) of C4-C12 diacids or diols optionally substituted with one or more hydroxyl groups; alkyl or aryl C1-C10 esters of glycerol, pentaerythritol, ethylene glycol, propylene glycol, as well as polyethoxylated derivatives of these and polyethylene glycol; C12-C22 alkyl esters or ethers of polypropylene; C12-C22 alkyl esters or ethers of polypropylene/polyethylene glycol copolymer.

Non-limiting examples of occlusive emollients include cyclic and linear dimethicones; polydialkylsiloxanes; polyarylalkylsiloxanes; long chain (C8-C36) alkyl and alkenyl esters of long straight or branched chain alkyl or alkenyl alcohols or acids; long chain (C8-C36) alkyl and alkenyl amides of long straight or branched chain (C8-C36) alkyl or alkenyl amines or acids; hydrocarbons including straight and branched chain alkanes and alkenes such as squalene, squalane and mineral oil; jojoba oil; polysiloxane polyalkylene copolymers; short chain alkyl or aryl esters (C1-C36) of C12-C22 diacids or diols optionally substituted with one or more hydroxyl groups such as diisopropyl dimer dilinoleate; and C12-C22 alkyl and alkenyl alcohols; long chain alkyl or aryl esters (C8-C36) of C12-C22 diacids or diols optionally substituted in available positions by —OH, such as diisostearyl dimer dilinoleate; lanolin and lanolin derivatives; and beeswax and its derivatives.

Non-limiting examples of humectant-type emollients include glycerol, polyglycerols (including: diglycerol, triglycerol, polyglycerin-3, tetraglycerol, hexaglycerol, decaglycerols), propylene glycol, dipropylene glycol, polypropylene glycol, polyethylene glycol (PEG-2 to PEG-45M, and in some embodiments, a molecular weight between about 300 and 1,000), sorbitol, polyhydric alcohol ethoxylates (e.g. sorbeth-6, sorbeth-30, glycereth-1 to glycereth-31), methoxides of polyethylene glycol (Methoxy PEG-2 to Methoxy PEG-100) methoxides of polyhydric alcohol ethoxylates (e.g. glycereth-7 methoxide), pantothenol, gluconic acid salts and the like. Other humectant-type agents that could also be employed include: 1,2,6-hexanetriol, acetamide MEA, aluminum hydroxide, arginine PEA, butoxypropanol, butylene glycol, dimethyl imidazolidinone, dimethylsilanol hyaluronate, dipotassium glycyrrhizate, erythritol, ethoxy-diglycol, fructose, glucamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-PEA, lactamide MEA, lactic acid, lactitol, lactose, lysine PEA, magnesium PEA, maltitol, manganese PEA, mannitol, Mel extract (honey extract), menthyl PEA, methyl gluceth-10, methyl gluceth-20, PEA (pidolic acid), lactamide, polydextrose, polyglucuronic acid, polyglyceryl sorbitol, potassium PEA, PPG-20 methyl glucose ether, PPG-38-buteth-37, saccharide isomerate, serica, silk amino acids, sodium carboxymethyl chitin, sodium lactate, sodium mannuronate methylsilanol, sodium PEA, sodium PEA methylsilanol, sodium polyglutamate, soluble collagen, sorbitol, sucrose, TEA-lactate, tea-PEA, trehalose, trilactin, urea, xylitol, Zea mays, zinc PEA, and combinations thereof.

The addition of one or more emollients may affect the viscosity and stability of the compositions of the present disclosure. In some embodiments, a single emollient may be added to the composition. In other embodiments, two or more emollients may be added to the composition. While any of a variety of emollients may be added to the formulations of the present disclosure, some embodiments will include wax and oil type emollients either alone or combined with water soluble emollients. In some embodiments of the disclosure, emollient systems can be comprised of humectants in addition to occlusive wax and oil emollients in concentrations that achieve a moisturizing effect and which maintain and improve the condition of the skin upon repeated use. Emollients may be non-comedogenic and chosen to avoid skin irritation or sensitization reactions.

M. Other Components

In one aspect, the composition or formulation additionally comprises an anti-oxidant. Non-limiting examples of antioxidants for use in the present disclosure include butylated hydroxytoluene, butylated hydroxyanisole, ascorbyl linoleate, ascorbyl dipalmitate, ascorbyl tocopherol maleate, calcium ascorbate, carotenoids, kojic acid and its pharmaceutically acceptable salts, thioglycolic acid and its pharmaceutically acceptable salts (e.g., ammonium), tocopherol, tocopherol acetate, tocophereth-5, tocophereth-12, tocophereth-18, or tocophereth-80.

In one aspect, the composition or formulation additionally comprises at least one preservative. Non-limiting examples of preservatives for use in the present disclosure include benzalkonium chloride, cetrimonium bromide (aka cetyltrimethylammonium bromide), cetylpyridinium chloride, benzethonium chloride, alkyltrimethylammonium bromide, methyl paraben, ethyl paraben, propyl paraben, butyl paraben, benzyl alcohol, cetyl alcohol, steryl alcohol, benzoic acid, sorbic acid, chloroacetamide, trichlorocarban, thimerosal, imidurea, bronopol, chlorhexidine, 4-chlorocresol, 4-chloroxylenol, dichlorophene and hexachlorophene. In some embodiments, the preservative is cetylpyridinium chloride, methyl paraben and propyl paraben, or mixtures thereof.

In still another aspect, the composition or formulation is acidic. In certain aspects, the composition or formulation has a pH of below about 7.5, 6.5, 5.5, 4.5, 3.5, or 2.5. In certain other aspects, the pH of composition or the formulation may range from about 1.5 to 7, about 2 to 7, about 3 to 7, about 4 to 7, or about 5 to 7. In still other aspects, the pH of the composition or formulation may range from about 1.5 to 5.5, about 2.5 to 5.5, about 3.5 to 5.5, or about 4.5 to 5.5. The composition or formulation may include a buffering agent to maintain its acidic pH. In some embodiments, the composition or formulation has a pH value between about 4 and 7.

In yet another aspect, the composition or formulation is basic. In certain aspects, the composition or formulation has a pH of above about 7, 8, 9, 10, 11, or 12. In certain other aspects, the pH of the composition or formulation may range from about 7 to 12.5, about 7 to 11.5, about 7 to 10.5, about 7 to 9.5, or about 7 to 8.5. In still other aspects, the pH of the composition or formulation may range from about 9 to 12.5, about 9 to 11.5, about 9 to 10.5, or about 8.5 to 10. The composition or formulation may include a buffering agent to maintain its basic pH. In some embodiments, the composition or formulation has a pH value between about 7 and 10.

In still yet another aspect, the composition or formulation is neutral. In certain aspects, the composition or formulation has a pH of about 7. In certain other aspects, the composition or formulation has a pH from about 6 to about 8.5, from about 5.5 to 8, about 6 to 8, about 6.5 to 8.5, or from about 6.5 to 7.5. The composition or formulation may include a buffering agent to maintain its neutral pH. In some embodiments, the composition or formulation has a pH value between about 6 and 8.5.

III. Characteristics

In still yet another embodiment of the present application, the composition or formulation is selected from a spray, a gel, a cream, an emulsion, a microemulsion, a lotion, an organogel, an ointment, a solution (e.g., a moderate to highly viscous solution), and a transdermal patch. In a further embodiment, the composition is a gel, for example, a low-viscosity gel, or a spray.

In certain other embodiments, the composition or formulation is designed for high penetration, for high retention in the skin, or for both high penetration and high retention. The optimal composition or formulation will have a balance between penetration and retention, enabling an effective amount of the active ingredient to pass through the skin, but also enabling it to stay in the target area for a sufficient duration to alleviate the patient's pain or other symptoms.

In another embodiment, the composition or formulation is designed for topical efficacy with minimal systemic distribution of the active through the body by the circulatory system (e.g., the cardiovascular system). The optimal composition or formulation will have low systemic bioavailability, but will effectively treat pain or other symptoms associated with the site of application.

In an alternative aspect, a composition or formulation comprising pregabalin has a flux (as determined by the finite dosing Franz cell procedure of Example 3) about equal to the flux of a known comparative formulation comprising pregabalin.

In another aspect, the composition or formulation flux is greater than the flux of the comparative formulation. In some embodiments, the composition or formulation flux is at least 1.5 times the flux of a comparative formulation. In other words, the ratio of (i) the flux of the composition or formulation comprising pregabalin to (ii) the flux of a comparative formulation with pregabalin is greater than 1.0 or at least about 1.5.

In some embodiments, the composition or formulation comprising pregabalin has a flux that is at least 2.0 times the flux of a comparative pregabalin formulation. In some embodiments, the composition or formulation has a flux that is at least 4.0 times the flux of a comparative formulation. In some embodiments, the composition or formulation has a flux that is at least 10.0 times the flux of a comparative formulation.

In another alternative aspect, the present disclosure provides a composition or formulation comprising pregabalin that provides a pregabalin flux (as determined by the Franz cell procedure of Example 3) of at least 0.7 µg hr$^{-2}$ at 24 hours, at least 1.1 0.7 µg hr$^{-1}$ cm$^{-2}$ at 24 hours, or at least 1.6 0.7 µg hr$^{-1}$ cm$^{-2}$ at 24 hours.

In still another embodiment, the composition or formulation comprising pregabalin has an enhancement ratio ("ER") of at least 1.5. In yet another embodiment, the composition or formulation comprising pregabalin has an ER of at least 2.0. In still another embodiment, the composition or formulation comprising pregabalin has an ER that is at least 5.0. In still another embodiment, the composition or formulation comprising pregabalin has an ER that is at least 10.0.

In still another embodiment, the composition or formulation comprising pregabalin provides additional advantages in comparison to previously described pregabalin compositions. Such advantages may include one or more of the following: adhering well to the skin, spreading easily, drying more quickly, and showing greater in vivo absorption. In some more specific embodiments, the drying rate of the formulation is less than 20 minutes.

In yet another embodiment, the composition or formulation of the present application is more viscous than water at standard temperature and pressure ("STP"). Alternatively, the composition has a kinematic viscosity of more than about 1 centistokes ("cSt") or a dynamic viscosity of more than about 1 centipoise (cP). In certain embodiments, the dynamic viscosity of the composition is at most about 2, 3, 4, 5, 7, 10, 12, 15, 20, 25, 30, 35, 40, 45, 50, 60, 70, 75, 80, 90, 100, 150, 200, 250, 500, 1000, 2000, 3000, 5000 or 10,000 cP at STP. In further embodiments, the dynamic viscosity is at most about 2, 3, 4, 5, 7, 10, 12, 15, 20, 25, 30, 35, 40, 45 or 50 cP at STP. In still further embodiments, the dynamic viscosity is at most about 2, 3, 4, 5, 7, 10, 12, 15 or 20 cP at STP. In yet other embodiments, the composition is thixotropic (i.e., it decreases in viscosity upon being stirred or shaken). The composition's viscosity can be adjusted by the addition of a thickening agent, such as a cellulosic thickening agent, for example, hydroxypropyl cellulose, or other thickening agents, or mixtures thereof.

In another embodiment, the composition is acidic. In certain embodiments, the composition has a pH of below about 7.5, of below about 6.5, of below about 5.5, of below about 4.5, of below about 3.5, or of below about 2.5. In certain other embodiments, the pH of the composition ranges from about 1.5 to about 7, about 2 to about 7, about 3 to about 7, about 4 to about 7, or about 5 to about 7, or is about 6.5.

In another embodiment, the composition is basic. In certain embodiments, the composition has a pH of above about 6.5, of above about 7.0, of above about 7.5, of above about 8.5, of above about 9.5, or of above about 10.5. In certain other embodiments, the pH of the composition ranges from about 7 to 11, about 7 to 10, or about 7 to 9, or is about 7.5.

In further embodiments, the composition or formulation remains stable for an acceptable time period between preparation and use when stored in a closed container at normal ambient temperature. In an embodiment, an "acceptable time period" is at least about 30 days, at least about six months, at least about one year, or at least about two years.

In an alternative embodiment, the present disclosure provides a composition or formulation that degrades by less than 1% over the course of 6 months at room temperature. In an embodiment, the rate of degradation is less than about 0.9, 0.8, 0.7, 0.6, 0.5, 0.4, 0.3, 0.2, or less than 0.1%, and all fractions in between, over the course of six months at room temperature.

In an alternative embodiment, the present disclosure provides a composition or formulation that when applied topically, that is to the skin exterior, facilitates the egress of one or more agents from the body for analysis or diagnostic purposes.

IV. Specific Compositions

In an embodiment of the present application, there is included a pharmaceutical composition comprising, consisting essentially of or consisting of pregabalin, water, DMSO, propylene glycol, levulinic acid, lauryl lactate, Brij L4, benzyl alcohol and cetylpyridinium chloride monohydrate ("CPC"). In some embodiments, the present application includes a pharmaceutical composition comprising, consisting essentially of or consisting of:
(a) about 1% w/w to about 5% w/w pregabalin;
(b) about 50% w/w to about 70% w/w water;
(c) about 10% w/w to about 20% w/w DMSO;
(d) about 5% w/w to about 15% w/w propylene glycol;
(e) about 1% w/w to about 3% w/w levulinic acid;
(f) about 1% w/w to about 3% w/w lauryl lactate;
(g) about 1% w/w to about 4% w/w Brij L4;
(h) about 1% w/w to about 2% w/w CPC.

In another embodiment of the present application, Brij L4 and CPC are omitted, dimethyl isosorbide is introduced, and water is in part replaced by ethanol. Accordingly, the present application includes a pharmaceutical composition comprising, consisting essentially of or consisting of:
(a) about 1% w/w to about 5% w/w pregabalin;
(b) about 5% w/w to about 25% w/w water;
(c) about 5% w/w to about 25% w/w ethanol;
(d) about 10% w/w to about 30% w/w DMSO;
(e) about 5% w/w to about 20% w/w propylene glycol;
(f) about 5% w/w to about 20% w/w dimethyl isosorbide;
(g) about 1% w/w to about 5% w/w levulinic acid;
(h) about 1% w/w to about 5% w/w lauryl lactate.

In another embodiment of the present application, propylene glycol is replaced by diisopropyl adipate and benzyl alcohol is introduced. Accordingly, the present application includes a pharmaceutical composition comprising, consisting essentially of or consisting of:
(a) about 1% w/w to about 5% w/w pregabalin;
(b) about 5% w/w to about 75% w/w water;
(c) about 5% w/w to about 25% w/w DMSO;
(d) about 5% w/w to about 20% w/w diisopropyl adipate;
(e) about 1% w/w to about 5% w/w benzyl alcohol;
(f) about 0.5% w/w to about 5% w/w levulinic acid;
(g) about 0.5% w/w to about 5% w/w lauryl lactate;
(h) about 1% w/w to about 4% w/w Brij L4;
(i) about 0.5% w/w to about 2% w/w CPC.

In another embodiment of the present application, benzyl alcohol is introduced. Accordingly, the present application includes a pharmaceutical composition comprising, consisting essentially of or consisting of:
(a) about 1% w/w to about 5% w/w pregabalin;
(b) about 45% w/w to about 75% w/w water;
(c) about 10% w/w to about 25% w/w DMSO;
(d) about 5% w/w to about 15% w/w propylene glycol;
(e) about 1% w/w to about 5% w/w benzyl alcohol;
(f) about 1% w/w to about 3% w/w levulinic acid;
(g) about 1% w/w to about 3% w/w lauryl lactate;
(h) about 1% w/w to about 4% w/w Brij L4;
(i) about 1% w/w to about 2% w/w CPC.

In another embodiment of the present application, benzyl alcohol is introduced and propylene glycol is replaced in part by dimethyl isosorbide. Accordingly, the present application includes a pharmaceutical composition comprising, consisting essentially of or consisting of:
(a) about 1% w/w to about 3% w/w pregabalin;
(b) about 40% w/w to about 75% w/w water;
(c) about 10% w/w to about 20% w/w DMSO;
(d) about 5% w/w to about 15% w/w propylene glycol;
(e) about 5% w/w to about 15% w/w dimethyl isosorbide;
(f) about 1% w/w to about 5% w/w benzyl alcohol;
(g) about 1% w/w to about 3% w/w levulinic acid;
(h) about 1% w/w to about 3% w/w lauryl lactate;
(i) about 1% w/w to about 3% w/w Brij L4;
(j) about 1% w/w to about 2% w/w CPC.

In some embodiments, the present application includes a pharmaceutical composition comprising, consisting essentially of or consisting of:
(i) about 1% w/w to about 5% w/w pregabalin;
(j) about 50% w/w to about 60% w/w water;
(k) about 20% w/w to about 30% w/w DMSO;
(l) about 5% w/w to about 10% w/w propylene glycol;
(m) about 1% w/w to about 5% w/w benzyl alcohol;
(n) about 1% w/w to about 5% w/w levulinic acid;
(o) about 1% w/w to about 5% w/w lauryl lactate;
(p) about 1% w/w to about 5% w/w Brij L4;
(q) about 1% w/w to about 4% w/w CPC.

In another embodiment of the present application, the DMSO concentration is somewhat reduced, and the water and propylene glycol contents are increased. Accordingly, the present application includes a pharmaceutical composition comprising, consisting essentially of or consisting of:
(i) about 1% w/w to about 5% w/w pregabalin;
(j) about 55% w/w to about 65% w/w water;
(k) about 10% w/w to about 20% w/w DMSO;
(l) about 7% w/w to about 15% w/w propylene glycol;
(m) about 1% w/w to about 5% w/w benzyl alcohol;
(n) about 1% w/w to about 5% w/w levulinic acid;
(o) about 1% w/w to about 5% w/w lauryl lactate;
(p) about 1% w/w to about 5% w/w Brij L4;
(q) about 1% w/w to about 4% w/w CPC.

In another embodiment of the present application, the benzyl alcohol is omitted. Accordingly, the present application includes a pharmaceutical composition comprising, consisting essentially of or consisting of:
(a) about 1% w/w to about 5% w/w pregabalin;
(b) about 55% w/w to about 65% w/w water;
(c) about 10% w/w to about 20% w/w DMSO;
(d) about 7% w/w to about 15% w/w propylene glycol;
(e) about 1% w/w to about 5% w/w levulinic acid;
(f) about 1% w/w to about 5% w/w lauryl lactate;
(g) about 1% w/w to about 5% w/w Brij L4;
(h) about 1% w/w to about 4% w/w CPC.

In another embodiment of the present application, propylene glycol is omitted, and dimethyl isosorbide is introduced. Accordingly, the present application includes a pharmaceutical composition comprising, consisting essentially of or consisting of:
(a) about 1% w/w to about 5% w/w pregabalin;
(b) about 55% w/w to about 65% w/w water;
(c) about 10% w/w to about 20% w/w DMSO;
(d) about 7% w/w to about 15% w/w dimethyl isosorbide;
(e) about 1% w/w to about 5% w/w benzyl alcohol;

(f) about 1% w/w to about 5% w/w levulinic acid;
(g) about 1% w/w to about 5% w/w lauryl lactate;
(h) about 1% w/w to about 5% w/w Brij L4;
(i) about 1% w/w to about 4% w/w CPC.

In another embodiment of the present application, propylene glycol is omitted, and diisopropyl adipate is introduced. Accordingly, the present application includes a pharmaceutical composition comprising, consisting essentially of or consisting of:
(a) about 1% w/w to about 5% w/w pregabalin;
(b) about 55% w/w to about 65% w/w water;
(c) about 10% w/w to about 20% w/w DMSO;
(d) about 7% w/w to about 15% w/w diisopropyl adipate;
(e) about 1% w/w to about 5% w/w benzyl alcohol;
(f) about 1% w/w to about 5% w/w levulinic acid;
(g) about 1% w/w to about 5% w/w lauryl lactate;
(h) about 1% w/w to about 5% w/w Brij L4;
(i) about 1% w/w to about 4% w/w CPC.

In another embodiment of the present application, DMSO is replaced in part by transcutol (2-(2-ethoxyethoxy)ethanol). Accordingly, the present application includes a pharmaceutical composition comprising, consisting essentially of or consisting of:
(a) about 1% w/w to about 5% w/w pregabalin;
(b) about 50% w/w to about 60% w/w water;
(c) about 10% w/w to about 20% w/w DMSO;
(d) about 5% w/w to about 10% w/w propylene glycol;
(e) about 1% w/w to about 5% w/w benzyl alcohol;
(f) about 1% w/w to about 5% w/w levulinic acid;
(g) about 1% w/w to about 5% w/w lauryl lactate;
(h) about 1% w/w to about 5% w/w Brij L4;
(i) about 1% w/w to about 4% w/w CPC
(j) about 7% w/w to about 15% w/w transcutol.

In a further embodiment of the present application, there is included a pharmaceutical composition comprising, consisting essentially of or consisting of pregabalin, water, DMSO, and CPC. Accordingly, the present application includes a pharmaceutical composition comprising, consisting essentially of or consisting of:
(a) about 1% w/w to about 5% w/w pregabalin;
(b) about 60% w/w to about 80% w/w water;
(c) about 10% w/w to about 30% w/w DMSO;
(d) about 1% w/w to about 5% w/w levulinic acid;
(e) about 1% w/w to about 4% w/w CPC.

In a further embodiment of the present application, lauryl lactate is also introduced. Accordingly, the present application includes a pharmaceutical composition comprising, consisting essentially of or consisting of:
(a) about 1% w/w to about 5% w/w pregabalin;
(b) about 60% w/w to about 80% w/w water;
(c) about 10% w/w to about 30% w/w DMSO;
(d) about 1% w/w to about 5% w/w levulinic acid;
(e) about 1% w/w to about 4% w/w CPC
(f) about 1% w/w to about 4% w/w lauryl lactate.

In a further embodiment of the present application, Brij L4 is also introduced. Accordingly, the present application includes a pharmaceutical composition comprising, consisting essentially of or consisting of:
(a) about 1% w/w to about 5% w/w pregabalin;
(b) about 60% w/w to about 80% w/w water;
(c) about 10% w/w to about 30% w/w DMSO;
(d) about 1% w/w to about 5% w/w levulinic acid;
(e) about 1% w/w to about 4% w/w CPC
(f) about 1% w/w to about 4% w/w oleyl alcohol
(g) about 2% w/w to about 5% w/w Brij L4.

In a further embodiment of the present application, oleyl alcohol is introduced in place of lauryl lactate. Accordingly, the present application includes a pharmaceutical composition comprising, consisting essentially of or consisting of:
(a) about 1% w/w to about 5% w/w pregabalin;
(b) about 60% w/w to about 80% w/w water;
(c) about 10% w/w to about 30% w/w DMSO;
(d) about 1% w/w to about 5% w/w levulinic acid;
(e) about 1% w/w to about 4% w/w CPC
(f) about 1% w/w to about 4% w/w oleyl alcohol.

In a further embodiment of the present application, Brij L4 is also introduced is also introduced. Accordingly, the present application includes a pharmaceutical composition comprising, consisting essentially of or consisting of:
(a) about 1% w/w to about 5% w/w pregabalin;
(b) about 60% w/w to about 80% w/w water;
(c) about 10% w/w to about 30% w/w DMSO;
(d) about 1% w/w to about 5% w/w levulinic acid;
(e) about 1% w/w to about 4% w/w CPC
(f) about 1% w/w to about 4% w/w oleyl alcohol
(g) about 2% w/w to about 5% w/w Brij L4.

In a further embodiment of the present application all compositions additionally comprise a thickening agent, in an amount of about 0.5% w/w to about 5.0% w/w, about 0.5% w/w to about 3.0% w/w, about 0.5% w/w to about 2.0% w/w, or about 1.5% w/w to about 2.5% w/w.

In a further embodiment of the present application all compositions additionally comprise at least one preservative, for example CPC, or methyl paraben and/or propyl paraben, in an amount of about 0.1% w/w to about 5.0% w/w, about 0.1% w/w to about 3.0% w/w or about 0.1% w/w to about 1.0% w/w.

V. Methods of Preparation

In some embodiments, the pharmaceutical compositions are formulated as a spray, cream, an emulsion, a microemulsion, a gel (e.g., a hydrogel, an organogel, an inorganic or silica gel, a high-viscosity gel or a low-viscosity gel), a lotion, a lacquer, an ointment, a solution (e.g., a moderate to highly viscous solution), or a transdermal patch. In a suitable embodiment, the composition is a gel, for example, a low-viscosity gel or a spray. Alternatively, the composition is a high-viscosity gel. The pharmaceutical composition of the present application may also be formulated as a transdermal patch. Low viscosity gels are, for example, gels having a dynamic viscosity in the range of about 400-4000 cP at STP. High viscosity gels are, for example, gels having a dynamic viscosity of at least 4000 cP at STP.

Methods of preparing compositions for topical administration are known in the art (see, for example, Remington's Pharmaceutical Sciences, 2000-20th edition, and The United States Pharmacopeia: The National Formulary, USP 24 NF19, published in 1999). In the present application compositions include those based on an aqueous or hydroalcoholic chassis. Therefore water soluble components are dissolved in the water phase and components soluble in the organic or alcohol phase are dissolved in the organic and/or alcohol phase and the two solutions, once homogeneous, are slowly combined and mixed to homogeneity with gentle heating and stirring, mixing or vortexing as needed. In another embodiment, all ingredients are combined directly and mixed to homogeneity with gentle heating and stirring, mixing or vortexing as needed.

VI. Methods of Treatment

Neuropathic pain, that is, pain caused by a lesion or disease of the somatosensory nervous system, presents a significant burden to individuals and to society by increasing disability and reducing productivity and quality of life, with concomitant increases in healthcare resource utilization and costs. Neuropathic pain, which may be either peripheral or central depending upon the site of the lesion within the nervous system, is characterized by a delayed onset of pain after nervous system lesion, pain in an area of sensory loss, spontaneous ongoing or paroxysmal pain, and evoked types of pain such as hyperalgesia or allodynia.

Estimates of the United States ("US") prevalence of neuropathic pain are 6-7%, corresponding to roughly 20M afflicted, although the estimate varies widely depending on the tools used to identify neuropathic pain and the estimate, as a result, likely reflects a lower bound. The most prevalent forms of neuropathic pain are diabetic peripheral neuropathy ("DPN"), cervical radiculopathy, carpal tunnel syndrome, and post herpetic neuralgia ("PHN"). Diabetes mellitus afflicts more than 25M persons in the US, of which an estimated 15% experience DPN, although other sources provide a still higher estimate. The lifetime risk of herpes zoster ("HZ"), also known as shingles, is upwards of 25% in the general population; nearly 1 million new HZ cases occur annually in the United States. Some 7-27% of HZ patients will experience PHN.

Peripheral neuropathic pain conditions are treated with a tricyclic antidepressant ("TCA"); duloxetine, a selective dual reuptake inhibitor of both serotonin and noradrenaline ("SNRI"); the anticonvulsants pregabalin and gabapentin; and a topical lidocaine patch. Other approaches to treat peripheral neuropathic pain conditions include use of opiates such as the synthetic opioid tramadol, morphine and oxycodone controlled release; membrane stabilizers; the antioxidant α-lipoic acid; topical capsaicin; certain antidepressant and antiepileptic medications; mexiletine; and N-methyl-d-aspartate ("NMDA") receptor antagonists. Percutaneous electrical nerve stimulation ("PENS") or transcutaneous electrical nerve stimulation ("TENS") have been used, and in extreme cases of DPN unresponsive to pharmacotherapy, occasional use of electrical spinal cord stimulation might be indicated.

Despite this slate of treatment options, peripheral neuropathic pain is often poorly managed and new, more effective and more convenient treatments are sorely needed.

Some embodiments provide for a method for treating a subject suffering from pain, said method comprising the topical administration to said subject of a therapeutically effective amount of a formulation as described herein.

In certain embodiments, the disclosure describes a method for treating pain in a subject comprising the step of applying a topical formulation to a subject to prevent or ameliorate pain, such as peripheral neuropathic pain.

In certain aspects, the pharmaceutical composition is applied to a limb or torso or other suitable body area of the subject. In some embodiments, the pharmaceutical composition is applied to the skin covering the tissue or tissues affected.

In other aspects, the subject is a human. Alternatively, the subject is a non-human mammal.

In still other aspects, the active agent alleviates pain. In some embodiments, the pain may be neuropathic pain. In some embodiments, the pain is DPN, cervical radiculopathy, carpal tunnel syndrome or PHN.

In yet still other aspects, the treatment is continued for at least one week, for one month, or for 12 weeks. In some embodiments, the treatment is continued for at least six months.

In one embodiment, the treatment may be administered once a day. In another embodiment, the treatment may be administered twice a day. In still another embodiment, the treatment may be administered three times a day. In yet another embodiment, the treatment may be administered four times a day. In some embodiments, the treatment is administered one to two times a day.

Formulation embodiments of the present disclosure are useful and effective when applied topically to treat a condition. The amount of the active agent present in the composition will be the amount that is therapeutically effective, i.e., an amount that will result in the effective treatment of the condition (e.g., DPN or PHN) when applied. The therapeutically effective amount will vary depending on the subject and the severity of the affliction and can be determined routinely by one of ordinary skill in the art.

In another aspect, the formulation comprising an active agent provides about equal flux (as determined by the Franz cell procedure of Example 3) as a comparative formulation containing the same active agent.

In another aspect, the formulation comprising an active agent provides better flux than a comparative formulation containing the same active agent. In some embodiments, the flux of the formulation is at least 1.5 times the flux of the comparative formulation's active. In other words, the ratio of (i) the formulation's active agent flux to (ii) the comparative formulation's active agent is greater than 1.0 or at least about 1.5. In some embodiments, the formulation has a flux that is at least 2.0 times greater than the flux of the comparative formulation. In some embodiments, the formulation has a flux that is at least 4.0 times greater than the comparative formulation's flux. In some embodiments, the formulation has a flux that is at least 10.0 times greater than the comparative formulation's flux.

In an alternative aspect, a formulation comprising pregabalin has a flux about equal to the flux of a known comparative formulation comprising pregabalin.

In another aspect, the composition flux is greater than the flux of the comparative formulation. In some embodiments, the composition flux is at least 1.5 times the flux of a comparative formulation. In other words, the ratio of (i) the flux of the composition comprising pregabalin to (ii) the flux of a comparative formulation with pregabalin is greater than 1.0 or at least about 1.5.

In some embodiments, the composition comprising pregabalin has a flux that is at least 2.0 times the flux of a comparative pregabalin formulation. In some embodiments, the composition has a flux that is at least 4.0 times the flux of a comparative formulation. In some embodiments, the composition has a flux that is at least 10.0 times the flux of a comparative formulation.

In another alternative aspect, the present disclosure provides a composition comprising pregabalin provides a pregabalin flux (as determined by the Franz cell procedure of Example 3) of at least 0.7 µg hr$^{-1}$ cm$^{-2}$ at 24 hours, at least 1.1 µg hr$^{-1}$ cm$^{-2}$ at 24 hours, or at least 1.6 µg hr$^{-1}$ cm$^{-2}$ at 24 hours.

The compositions of the disclosure are suitable for use on mammalian skin.

VII. Dispensing System

Compositions of the present disclosure may, if desired, be presented in a pouch, bottle, pump bottle, spray bottle, foaming dispenser or other closure system approved by the US Food and Drug Administration ("FDA") or other regulatory body, which may contain one or more unit dosage forms containing the active ingredient. The bottle or dispenser may also be accompanied by a notice associated with the container in a form prescribed by a governmental agency regulating the manufacture, use, or sale of pharmaceuticals, the notice indicating approval by the agency.

In some aspects, the compositions of the present disclosure may be formulated into products that can be dispensed from a reservoir using a release assembly (e.g., a hand pump) to dispense an amount of the composition whenever the release assembly is put into action. The amount of the composition dispensed by the pump may or may not be metered to dispense a consistent amount of formulation.

EXAMPLES

Example 1

General Procedure for Formulation Preparation

A desired weight of an active agent, such as pregabalin, is weighed in a glass media bottle. DMSO, water and the alcohols are introduced. The media bottle is capped and the contents sonicated at room temperature until the active agent is fully dissolved. The remaining excipients are then added and the resulting mixture are then briefly mixed until a clear, homogeneous solution is obtained.

Example 2

Exemplary Formulations

Formulations of compositions as provided in Tables 1-6 (amounts shown as % w/w) were prepared using the general procedure described under Example 1.

TABLE 1

Exemplary pregabalin formulation compositions

|  | TrPg108-2 | TrPg200 | TrPg107-2 | TrPg201 | TrPg101-2 | TrPg202 | TrPg204 | TrPg205 | TrPg206 |
|---|---|---|---|---|---|---|---|---|---|
| Pregabalin | 2.50 | 2.50 | 2.50 | 2.50 | 2.45 | 2.50 | 2.49 | 2.49 | 2.49 |
| Ethanol |  |  |  |  | 24.51 | 20.00 | 9.95 | 19.90 | 19.90 |
| Water | 95.50 | 95.50 | 93.50 | 93.50 | 69.12 | 45.00 | 59.70 | 24.88 | 19.90 |
| Cetylpyridinium chloride mono-hydrate | 2.00 | 2.00 | 2.00 | 2.00 | 1.96 |  |  |  |  |
| Levulinic acid |  |  | 2.00 | 2.00 | 1.96 |  |  |  | 2.99 |
| DMSO |  |  |  |  |  | 14.50 | 14.93 | 29.85 | 19.90 |
| Dimethyl isosorbide |  |  |  |  |  |  | 4.98 | 4.98 | 14.93 |
| Propylene glycol |  |  |  |  |  | 7.50 | 4.98 | 9.95 | 16.92 |
| Glycerin |  |  |  |  |  | 2.50 |  |  |  |
| Lauryl lactate |  |  |  |  |  |  |  | 3.98 | 2.99 |
| Benzyl alcohol |  |  |  |  |  | 2.00 |  |  |  |
| Brij S20 |  |  |  |  |  | 3.00 |  |  |  |
| Brij L4 (30) |  |  |  |  |  | 3.00 | 2.99 | 3.98 |  |

TABLE 2

Exemplary pregabalin formulation compositions

|  | TrPg207 | TrPg208 | TrPg209 | TrPg210 | TrPg218 | TrPg219 |
|---|---|---|---|---|---|---|
| Pregabalin | 1.95 | 1.75 | 1.71 | 1.68 | 1.70 | 1.48 |
| Ethanol |  |  |  |  |  |  |
| Water | 73.05 | 65.38 | 64.04 | 62.75 | 63.61 | 55.33 |
| Cetyl-pyridinium chloride monohydrate | 1.56 | 1.40 | 1.37 | 1.34 | 1.36 | 1.18 |

TABLE 2-continued

Exemplary pregabalin formulation compositions

|  | TrPg207 | TrPg208 | TrPg209 | TrPg210 | TrPg218 | TrPg219 |
|---|---|---|---|---|---|---|
| Levulinic acid | 1.56 | 1.40 | 1.37 | 1.34 |  | 1.18 |
| DMSO | 19.53 | 17.48 | 17.12 | 16.78 | 17.01 | 26.63 |
| Propylene glycol |  | 10.49 | 10.27 | 10.07 | 10.20 | 8.88 |
| Lauryl lactate |  |  | 2.05 | 2.01 | 2.04 | 1.78 |
| Benzyl alcohol |  |  |  | 2.01 | 2.04 | 1.78 |
| Brij L4 (30) | 2.34 | 2.10 | 2.05 | 2.01 | 2.04 | 1.78 |

TABLE 3

Exemplary pregabalin formulation compositions

|  | TrPg209 | TrPg210 | TrPg211 | TrPg212 | TrPg220 |
|---|---|---|---|---|---|
| Pregabalin | 1.71 | 1.68 | 1.68 | 1.68 | 1.48 |
| Water | 64.04 | 62.75 | 62.75 | 62.75 | 55.33 |
| Cetylpyridinium chloride monohydrate | 1.37 | 1.34 | 1.34 | 1.34 | 1.18 |
| Levulinic acid | 1.37 | 1.34 | 1.34 | 1.34 | 1.18 |
| DMSO | 17.12 | 16.78 | 16.78 | 16.78 | 14.79 |
| Dimethyl isosorbide |  |  | 10.07 |  |  |
| Propylene glycol | 10.27 | 10.07 |  |  | 8.88 |
| Diisopropyl adipate |  |  |  | 10.07 |  |
| Lauryl lactate | 2.05 | 2.01 | 2.01 | 2.01 | 1.78 |
| Transcutol |  |  |  |  | 11.83 |
| Benzyl alcohol |  | 2.01 | 2.01 | 2.01 | 1.78 |
| Brij L4 (30) | 2.05 | 2.01 | 2.01 | 2.01 | 1.78 |

TABLE 4

Exemplary pregabalin formulation compositions

|  | TrPg202 | TrPg204 | TrPg206 | TrPg217 | TrPg219 |
|---|---|---|---|---|---|
| Pregabalin | 2.50 | 2.49 | 2.49 | 1.68 | 1.48 |
| Ethanol | 20.00 | 9.95 | 19.90 |  |  |
| Water | 45.00 | 59.70 | 19.90 | 62.75 | 55.33 |
| Cetylpyridinium chloride monohydrate |  |  |  | 1.34 | 1.18 |
| Levulinic acid |  |  | 2.99 | 1.34 | 1.18 |
| DMSO | 14.50 | 14.93 | 19.90 | 16.78 | 26.63 |

TABLE 4-continued

Exemplary pregabalin formulation compositions

|  | TrPg202 | TrPg204 | TrPg206 | TrPg217 | TrPg219 |
|---|---|---|---|---|---|
| Dimethyl isosorbide |  | 4.98 | 14.93 |  |  |
| Propylene glycol | 7.50 | 4.98 | 16.92 | 10.07 | 8.88 |
| Glycerin | 2.50 |  |  |  |  |
| Lauryl lactate |  |  | 2.99 | 2.01 | 1.78 |
| Benzyl alcohol | 2.00 |  |  | 2.01 | 1.78 |
| Brij S20 | 3.00 |  |  | 2.01 |  |
| Brij L4 (30) | 3.00 | 2.99 |  |  | 1.78 |

TABLE 5

Exemplary pregabalin formulation compositions

|  | TrPg210 | TrPg213 | TrPg215 |
|---|---|---|---|
| Pregabalin | 1.68 | 1.66 | 1.71 |
| Water | 62.75 | 62.13 | 64.04 |
| Cetylpyridinium chloride monohydrate | 1.34 | 1.33 |  |
| Levulinic acid | 1.34 | 1.33 |  |
| DMSO | 16.78 | 16.61 | 17.12 |
| Propylene Glycol | 10.07 | 9.97 | 10.27 |
| Lauryl lactate | 2.01 | 1.99 | 2.05 |
| Benzyl Alcohol | 2.01 | 1.99 | 2.05 |
| Brij L4 (30) | 2.01 | 1.99 | 2.05 |
| HY117 |  | 1.00 |  |
| Carbopol 971 |  |  | 0.68 |

TABLE 6

Exemplary pregabalin formulation compositions

|  | TrPg300 | TrPg301 | TrPg302 | TrPg303 | TrPg304 | TrPg305 | TrPg306 | TrPg307 | TrPg308 |
|---|---|---|---|---|---|---|---|---|---|
| Pregabalin | 2.60 | 2.55 | 2.50 | 2.00 | 1.94 | 1.95 | 1.95 | 1.92 | 1.89 |
| Water | 97.40 | 95.41 | 93.50 | 74.80 | 72.48 | 73.05 | 73.05 | 71.92 | 70.83 |
| Cetylpyridinium chloride monohydrate |  | 2.04 | 2.00 | 1.60 | 1.55 | 1.56 | 1.56 | 1.54 | 1.52 |
| Levulinic acid |  |  | 2.00 | 1.60 | 1.55 | 1.56 | 1.56 |  | 1.52 |
| DMSO |  |  |  | 20.00 | 19.38 | 19.53 | 19.53 | 19.23 | 18.94 |
| Lauryl lactate |  |  |  |  |  | 2.34 |  |  |  |
| Brij L4 (30) |  |  |  |  | 3.10 |  |  | 3.08 | 3.03 |
| Oleyl Alcohol |  |  |  |  |  |  | 2.34 | 2.31 | 2.27 |

Example 3

Skin Permeation Measurement

Franz diffusion cell experiments were used to analyze flux rates of pregabalin from compositions taught under the present disclosure across a substrate membrane. Franz diffusion cells are a common and well known method for measuring transdermal flux rates. The general Franz cell procedure is described by Franz (J. Invest. Dermatol., 1975, 64, 190-195).

In the present examples, Franz diffusion cells ("FDC"s) with a 3.3 mL receptor well volume were used with split thickness human cadaver skin (0.015"-0.018", AlloSource or New York Firefighters Tissue Bank). The donor well had an area of about 0.55 cm$^2$. The receptor wells were filled with isotonic phosphate-buffered saline solution ("PBS") doped with 0.01% sodium azide. The receptor wells of the FDCs were maintained at 37° C. (the temperature on the surface of the skin is 32° C.) in a stirring dry block with continual agitation via a stir bar. The flanges of the Franz cells were coated with vacuum grease to ensure a complete seal and donor and receptor chambers were clamped about the skin piece under uniform pressure using a pinch clamp (SS #18 VWR 80073-350).

After the FDCs were assembled, the skin was allowed to hydrate for 20 minutes in contact with the receptor fluid. Any FDCs that evidenced any leakage during this period were discarded. The integrity and quality of each skin piece was tested prior to application of the test formulations through measurement of the transdermal flux of tritiated water. Skin pieces evidencing an excessively high tritiated water flux were discarded and the tritiated water fluxes of accepted skin pieces were used to guide the distribution of test formulation samples over the skin piece set. After removal of the tritiated water samples from the donor wells, the clamps and donor wells were removed. The skin was tapped dry with a KimWipe and the receptor well solutions were replenished with fresh receptor well medium. The donor wells and clamps were then re-applied.

Six replicates of each of the test formulations are examined, typically in a batch of some 36 FDCs in total. Each test formulation was applied at a finite dose of 5 μL (9 mg cm$^{-2}$) on skin maintained at 32° C. throughout the experiments. The Receptor Fluid was stirred with a magnetic stir bar throughout. A sample was abstracted from each receptor well at preset times, typically 4 h and 22 h or 24 h, the receptor well-being replenished with fresh receptor fluid. The concentration of pregabalin in each receptor well sample was assayed by a verified high-performance liquid chromatography ("HPLC") or liquid-chromatography—mass spectrometry ("LC-MS") analytical method.

At the end of the experiment (22 h or 24 h), residual formulation was removed from the skin exterior with a pipette. The FDC was disassembled and the skin washed twice with EtOH-Water 50-50 and wiped dry with a Kim-Wipe. The successive topmost layers of the stratum corneum are removed by three (3) times applying cellophane tape to the skin and then pulling off the tape. Tape strippings were discarded, the material present in those peripheral layers being considered absorbed only superficially. The epidermal and dermal layers were separated, using mild heating if required. The epidermal and dermal sections were placed into 4 ml glass vials. 2 ml of extraction solvent was added to each vial and the vials allowed to incubate for 24 h. At the end of the extraction period, aliquots of the extraction solvent were drawn, filtered and analyzed. Measurements were made in six-fold replicates. The concentration of pregabalin in the samples was analyzed the verified HPLC or LC-MS method.

Figure 5A:
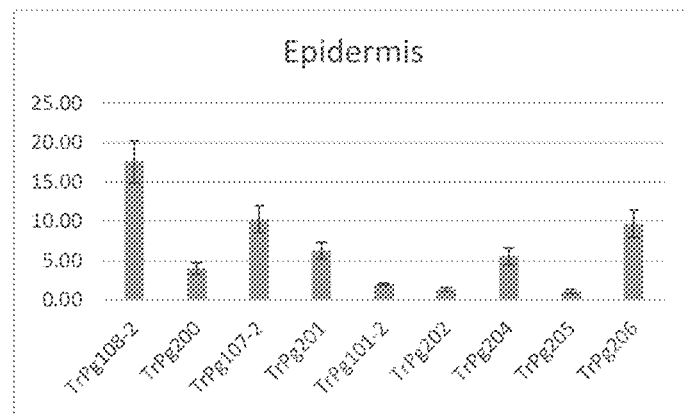
FIG. 5A to FIG. 5C illustrates cumulative amounts of pregabalin that are found to permeate through human skin (FIG. 5C) and to be retained in human epidermal tissue (FIG. 5A) and in human dermal tissue (FIG. 5B) over a period of 20 or 24 hours from the formulations of Table 1 (the numbers for formulations TrPg200 and TrPg201 represent unweighted averages of results from, respectively, two and four independent runs according to the procedure of Example 3).
Figure 5B:
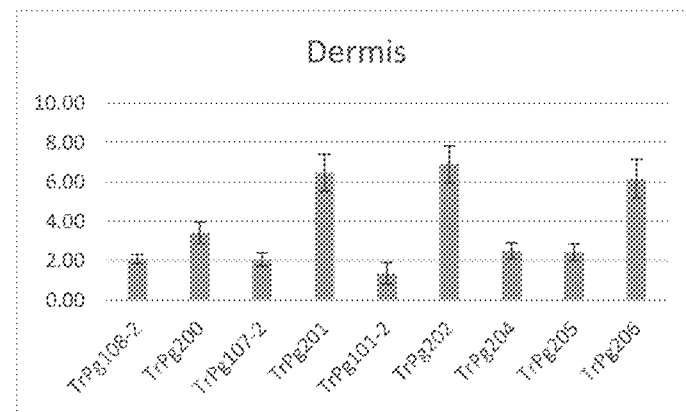
Figure 5C:
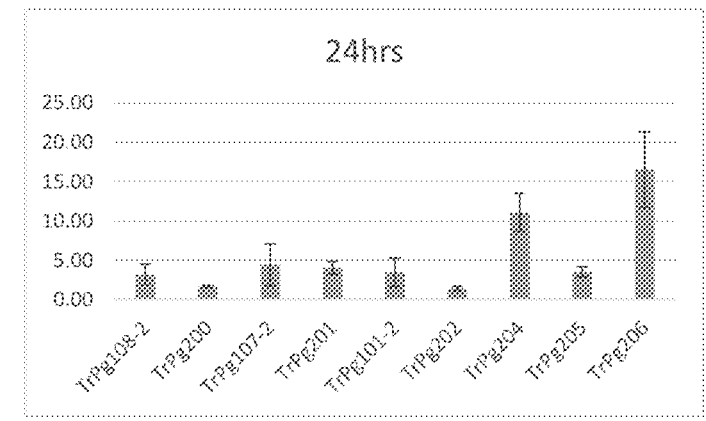
Figure 6A:
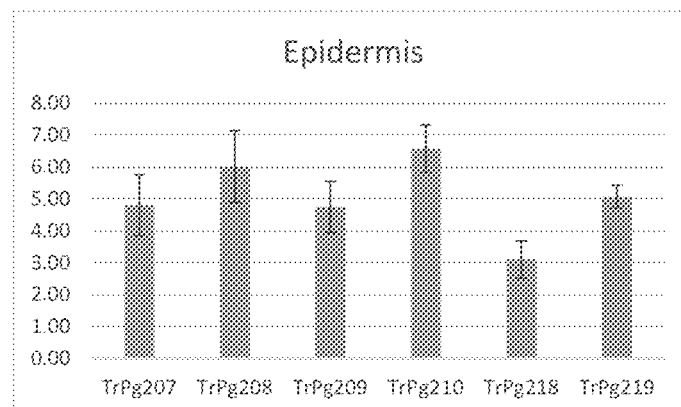
FIG. 6A to FIG. 6C illustrates cumulative amounts of pregabalin that are found to permeate through human skin (FIG. 6C) and to be retained in human epidermal tissue (FIG. 6A) and in human dermal tissue (FIG. 6B) over a 22 hour period from formulations of Table 2 (dermal retention numbers were not measured for formulations TrPg218 and TrPg219; the numbers for formulation TrPg210 represent unweighted averages of results from three independent runs according to the procedure of Example 3).
Figure 6B:
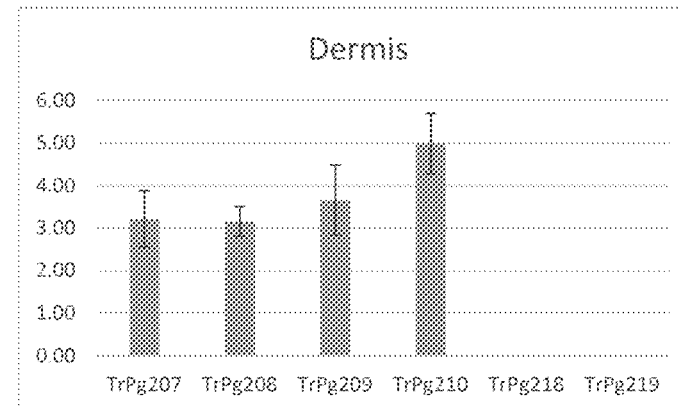
Figure 6C:
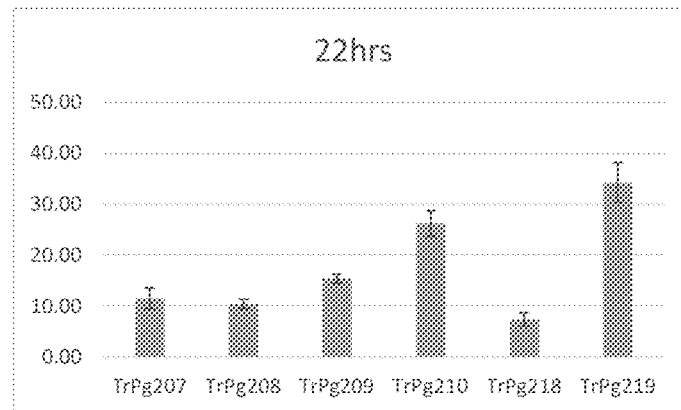
Figure 7A:
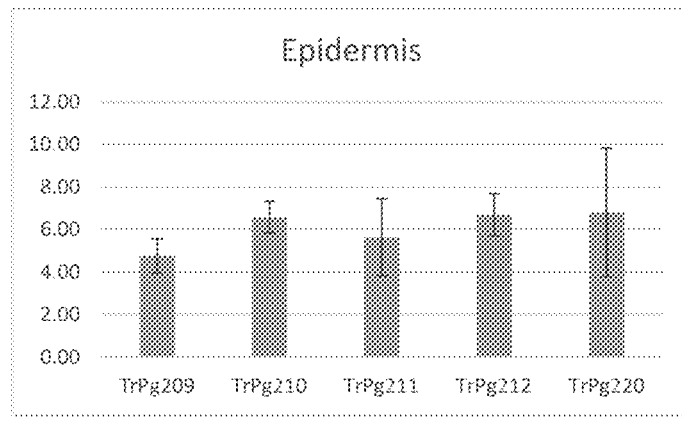
FIG. 7A to FIG. 7C illustrates cumulative amounts of pregabalin that are found to permeate through human skin (FIG. 7C) and to be retained in human epidermal tissue (FIG. 7A) and in human dermal tissue (FIG. 7B) over a 22 hour period from the formulations of Table 3 (dermal retention numbers were not measured for formulation TrPg220; the numbers for formulation TrPg210 represent unweighted averages of results from three independent runs according to the procedure of Example 3).
Figure 7B:
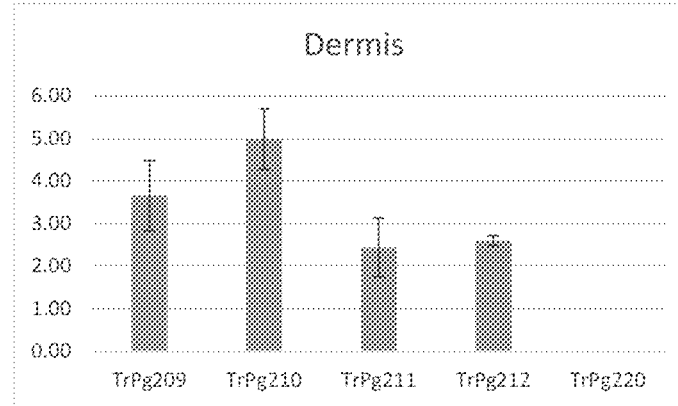
Figure 7C:
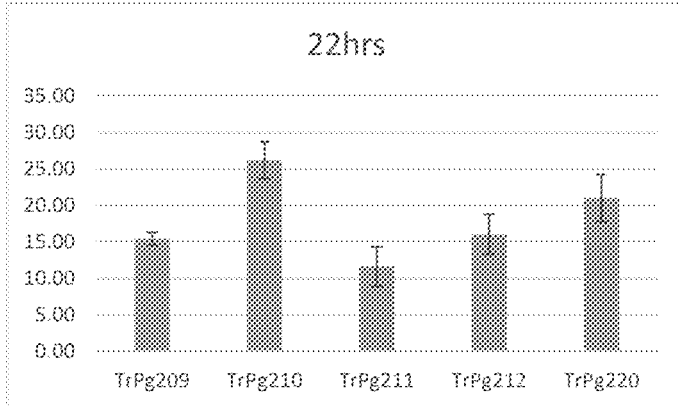
Figure 8A:
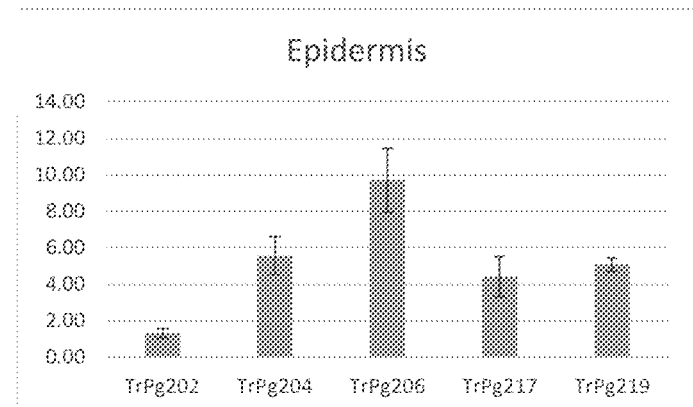
FIG. 8A to FIG. 8C illustrates cumulative amounts of pregabalin that are found to permeate through human skin (FIG. 8C) and to be retained in human epidermal tissue (FIG. 8A) and in human dermal tissue (FIG. 8B) over a period of 20 or 22 hours from the formulations of Table 4 (dermal retention numbers were not measured for formulations TrPg217 and TrPg219).
Figure 8B:
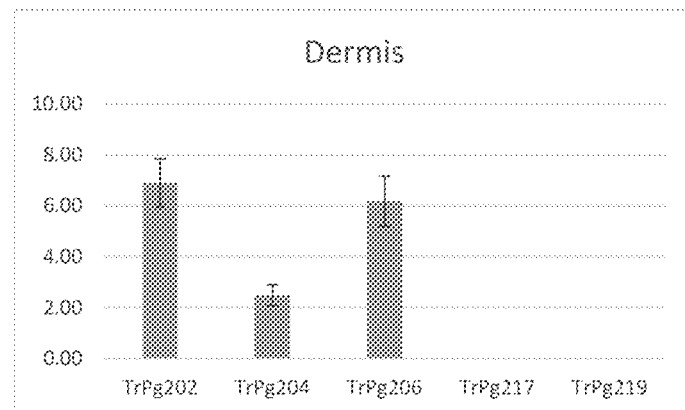
Figure 8C:
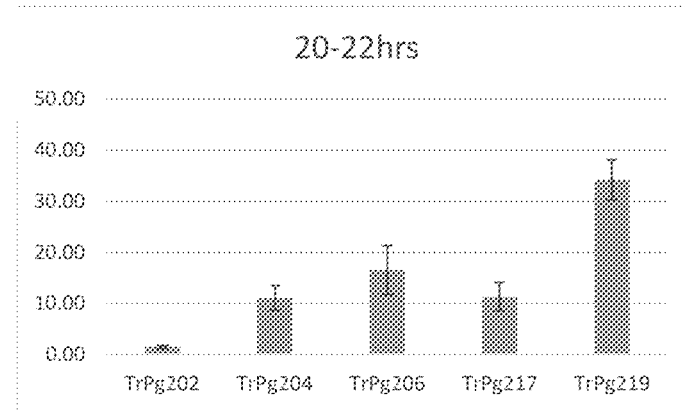
Figure 9A:
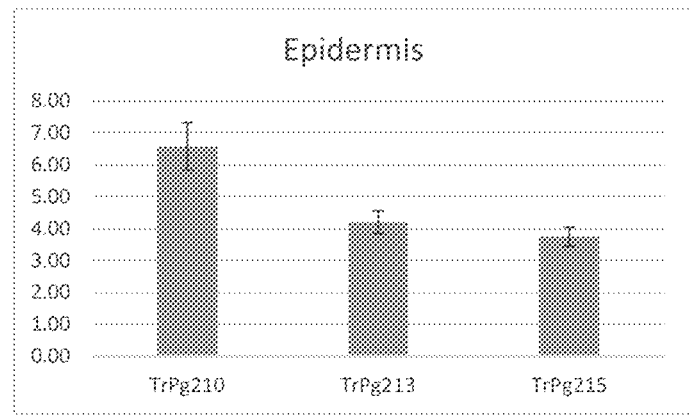
FIG. 9A to FIG. 9C illustrates cumulative amounts of pregabalin that are found to permeate through human skin (FIG. 9C) and to be retained in human epidermal tissue (FIG. 9A) and in human dermal tissue (FIG. 9B) over a 22 hour period from the formulations of Table 5 (the numbers for formulation TrPg210 represent unweighted averages of results from three independent runs according to the procedure of Example 8).
Figure 9B:
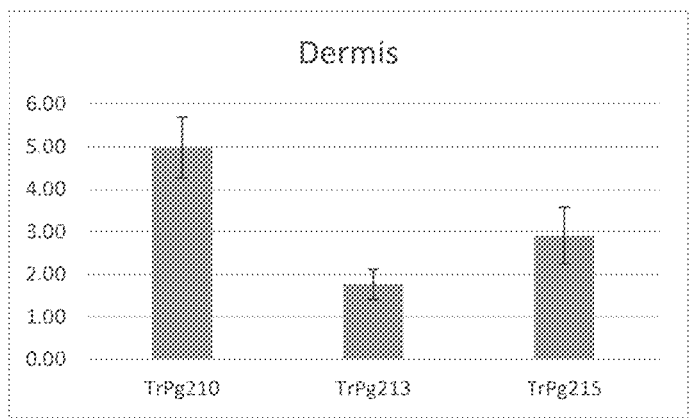
Figure 9C:
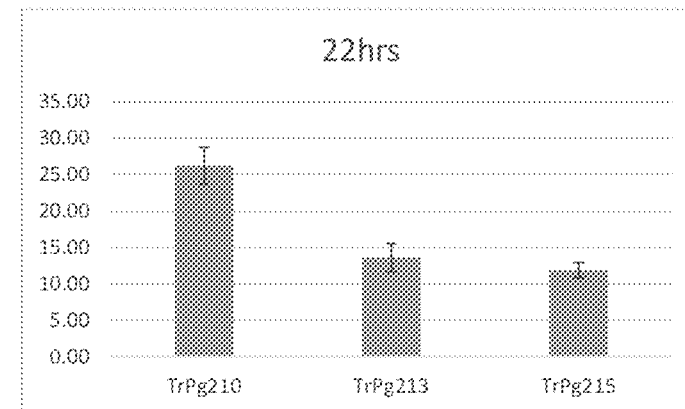
Figure 10A:
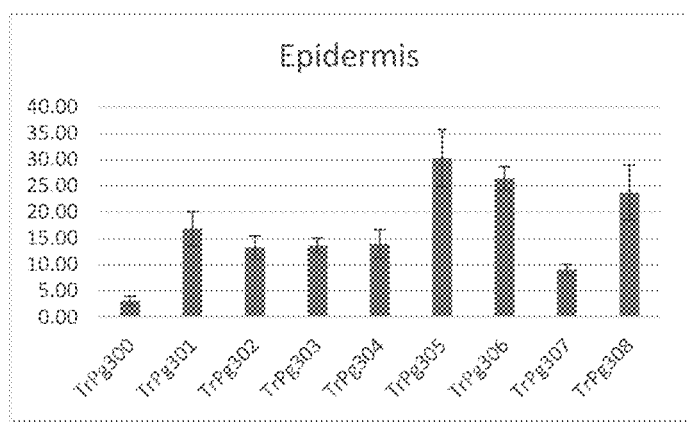
FIG. 10A to FIG. 10D illustrates cumulative amounts of pregabalin that are found to permeate through human skin over a 4 hour period (FIG. 10C) and over a 24 hour period (FIG. 10D) and to be retained over a 24 hour period in human epidermal tissue (FIG. 10A) and in human dermal tissue (FIG. 10B) from the formulations described in Table 6.
Figure 10B:
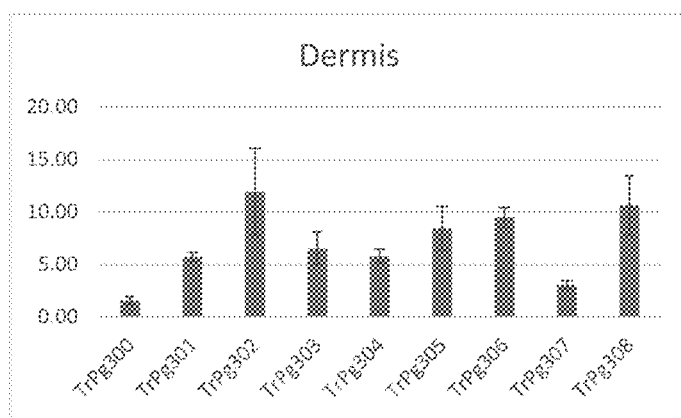
Figure 10C:
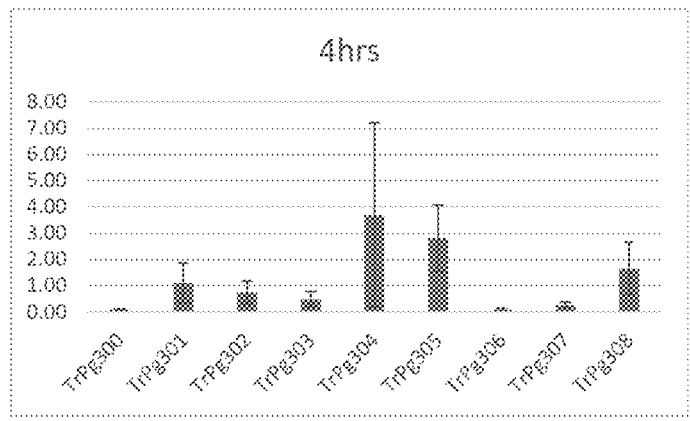
Figure 10D:
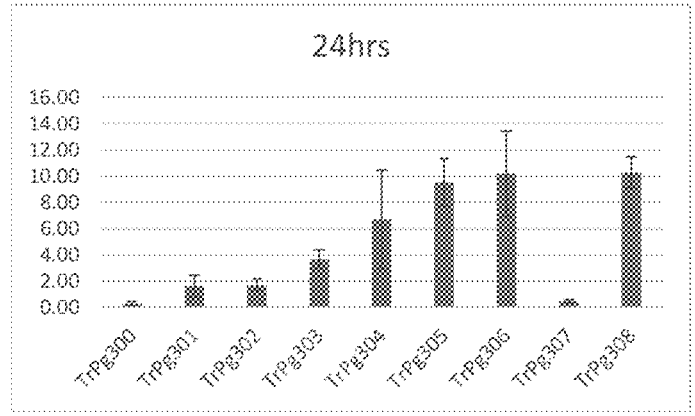

Measurements of the permeation of pregabalin through and retention of pregabalin in the epidermal and dermal compartments of human cadaver skin were made according to the above procedure. The results are provided in FIGS. 1 to 10D. Numbered formulations "PreG" of FIGS. 1-4 correspond to formulations "TrPg" of Tables 1-5 above. Additionally, FIG. 5A to 5C summarizes the data from formulations of Table 1, FIG. 6A to 6C summarizes the data from formulations of Table 2, FIG. 7A to 7C summarizes the data from formulations of Table 3, FIG. 8A to 8C summarizes the data from formulations of Table 4, FIG. 9A to 9C summarizes the data from formulations of Table 5, and FIG. 10A to 10D summarizes the data from formulations of Table 6.

Comparing results for TrPg210 (for which results from three independent skin permeation studies (the average of which is plotted in FIG. 7A to 7C) provide average enhancement ration of 2.1 (3); 8.1 (7); 1.3 (1) for each of 4 h, 24 h and epidermis respectively), with those for TrPg 217 (for which the corresponding numbers are 1.1 (4); 3.1 (8); 1.4 (3)). It is contemplated that the smaller polyethylene glycol alkyl ether, Brij L4 (polyethylene glycol dodecyl ether also termed polyoxyethylene (4) lauryl ether; $(C_2H_4O)nC_{12}H_{26}O$; $n_{average}$=4, average molecular weight 362) contributes substantially more to increased pregabalin flux than the larger Brij S20 (polyoxyethylene monooctadecyl ether, also termed polyoxyethylene (20) stearyl ether, formerly termed Brij™ 78; $C_{18}H_{37}(OCH_2CH_2)nOH$, n~20, average molecular weight 1,152).

It is understood that the examples and embodiments described herein are for illustrative purposes only. Various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A topical formulation comprising: (i) about 1% w/w to about 5% w/w pregabalin, (ii) water, (iii) 10% to 20% w/w dimethyl sulfoxide ("DMSO"), (iv) about 0.5 % to about 5% w/w levulinic acid, (v) about 0.5% to about 5% w/w lauryl lactate, (vi) about 5% to about 15% w/w propylene glycol, and (vii) about 1% to about 4% polyethylene glycol dodecyl ether.

2. The topical formulation of claim 1, further comprising cetylpyridinium chloride.

3. The topical formulation of claim 1, further comprising dimethyl isosorbide.

4. The topical formulation of claim 1, further comprising a monohydric alcohol.

5. The topical formulation of claim 1, comprising about 50% to about 70% water.

6. The topical formulation of claim 1, comprising about 1% to about 3% w/w levulinic acid.

7. The topical formulation of claim 1, comprising about 1% to about 3% w/w lauryl lactate.

8. The topical formulation of claim 1, comprising about 12% to about 20% w/w DMSO.

9. The topical formulation of claim 2, comprising about 1% to about 2% cetylpyridinium chloride.

* * * * *